(12) United States Patent
McSweeney et al.

(10) Patent No.: US 12,105,730 B2
(45) Date of Patent: Oct. 1, 2024

(54) METHODS, MEDIUMS, AND SYSTEMS FOR UPLOADING AND VISUALIZING DATA IN AN ANALYTICAL ECOSYSTEM

(71) Applicant: Waters Technologies Ireland Limited, Dublin (IE)

(72) Inventors: Romuald McSweeney, Uxbridge, MA (US); Steven Cohn, Franklin, MA (US); Matthew Buehler, Blackstone, MA (US)

(73) Assignee: Waters Technologies Ireland Limited, Dublin (IE)

( * ) Notice: Subject to any disclaimer, the term of this patent is extended or adjusted under 35 U.S.C. 154(b) by 0 days.

(21) Appl. No.: 18/052,309

(22) Filed: Nov. 3, 2022

(65) Prior Publication Data

US 2023/0135177 A1    May 4, 2023

Related U.S. Application Data

(60) Provisional application No. 63/275,593, filed on Nov. 4, 2021.

(51) Int. Cl.
*G06F 16/00* (2019.01)
*G06F 16/21* (2019.01)
(Continued)

(52) U.S. Cl.
CPC ............ *G06F 16/26* (2019.01); *G06F 16/214* (2019.01); *G06F 16/254* (2019.01); *G06F 16/256* (2019.01); *G06F 16/904* (2019.01)

(58) Field of Classification Search
CPC ...... G06F 16/26; G06F 16/256; G06F 16/214; G06F 16/254; G06F 16/904
(Continued)

(56) References Cited

U.S. PATENT DOCUMENTS 10,980,491 B1 *  4/2021  Jones .................... A61B 5/7275
2012/0023429 A1 *  1/2012  Medhi ................. G06F 3/04842
                                                715/772
(Continued)

FOREIGN PATENT DOCUMENTS

WO      2022215053  A1   10/2022

OTHER PUBLICATIONS

International Search Report and Written Opinion for International Patent Application No. PCT/IB2022/060606, mailed Feb. 3, 2023.
(Continued)

*Primary Examiner* — Chelcie L Daye
(74) *Attorney, Agent, or Firm* — Goodwin Procter LLP

(57) ABSTRACT

Exemplary embodiments provide computer-implemented methods, mediums, and apparatuses configured to visualize data stored in a cloud-based storage service. A database in the data storage ecosystem may store results sets from an analytical chemistry system. An uploader may automatically upload the data into cloud storage. Because a great deal of data can be made available this way, more complex analyses can be performed based on visualizations for the data. Examples of analyses performed in connection with these visualizations include product analyses for potency and stability, analyst performance analyses, analytical method analyses, site performance analyses, etc.

20 Claims, 19 Drawing Sheets

(51) Int. Cl.
  *G06F 16/25*  (2019.01)
  *G06F 16/26*  (2019.01)
  *G06F 16/904*  (2019.01)

(58) Field of Classification Search
  USPC .......................................................... 707/722
  See application file for complete search history.

(56) References Cited

U.S. PATENT DOCUMENTS

2015/0040047 A1*  2/2015  Baarz ................... G06F 16/904
                                                                          715/769
2020/0158697 A1*  5/2020  Jensen ................... H01J 49/26

OTHER PUBLICATIONS

Douglas, S. E., "The Complete Guide to LIMS & Laboratory Informatics Contents 2015 Edition", Mar. 23, 2015, Retrieved from the Internet: URL:https://kupdf.net/download/the-complete-guide-to-lims-amp-laboratory-informatics-2015 edition_58e53be2dc0d60f027da981e_pdf, [retrieved on Feb. 12, 2019].

Bauch, A., et al., "openBIS: a flexible framework for managing and analyzing complex data in biology research", BMC Bioinformatics, 12(1):468, Dec. 8, 2011.

Anonymous, "AWS Glue Developer Guide—first 400 pages", Oct. 19, 2020, Retrieved from the Internet: URL:https://web.archive.org/web/20201019205956if_/https://docs.aws.amazon.com/glue/latest/dg/glue-dg.pdf, [retrieved on Mar. 3, 2022].

International Preliminary Report on Patentability for International Patent Application No. PCT/IB2022/060606, mailed May 16, 2024.

* cited by examiner

METHODS, MEDIUMS, AND SYSTEMS FOR UPLOADING AND VISUALIZING DATA IN AN ANALYTICAL ECOSYSTEM

CROSS-REFERENCE TO RELATED APPLICATIONS

This application claims the benefit of and priority to U.S. Provisional Patent Application No. 63/275,593, filed Nov. 4, 2021. The entire disclosure of which is hereby incorporated by reference.

BACKGROUND

Laboratory analytical instruments are devices for qualitatively and/or quantitatively analyzing samples. They are often used in a laboratory setting for scientific research or testing. Such devices may measure the chemical makeup of a sample, the quantity of components in a sample, and perform similar analyses. Examples include mass spectrometers, chromatographs, titrators, spectrometers, elemental analyzers, particle size analyzers, rheometers, thermal analyzers, etc.

When analyzing data from laboratory analytical instruments, it may be desirable to consider results across multiple different data sets. Moreover, it may be more convenient to access instrument data from a centralized source, such as cloud storage.

However, moving multiple data sets or instrument data to a new storage location can be difficult. Among other problems, data may exist within a data ecosystem that serializes the data based on a set of libraries. In addition to making the data easier to store (generally in a proprietary format), the libraries may also define derived channels in the data (whose values may not be explicitly stored in the data set but are derived from data that is).

In order to move analytical data to a new location, the libraries typically need to be used to deserialize the data and generate derived channels. This can be accomplished by using an interface into the data ecosystem. Calling the interface commands may invoke the libraries within the data ecosystem and return deserialized data.

However, calling into the interface can be a slow process because the data ecosystem often supports additional components, such as security systems and auditing protocols, which may not be necessary when a user only wishes to transfer existing data from one place to another. Thus, a large number of processes may need to be run unnecessarily, slowing down the data transfer. Furthermore, existing data ecosystems are often run in a single-threaded process, so uploading data via the ecosystem competes for ecosystem resources. Another problem is that this somewhat cumbersome process needs to be repeated every time a user acquires new data that they wish to store in the centralized location.

BRIEF SUMMARY

Exemplary embodiments relate to improved techniques for transferring analytical chemistry data to a centralized location. One advantage of the techniques described herein is that they can quickly aggregate large amounts of data across multiple data sets. This allows for new options for visualizing the data and identifying trends across the data sets.

Exemplary embodiments may include computer-implemented methods, as well as non-transitory computer-readable mediums storing instructions for performing the methods, apparatuses configured to perform the methods, etc.

In one embodiment, a computer-implemented method includes accessing a database for a data ecosystem storing one or more results sets according to a first model structure. A data ecosystem may be a set of computing resources that collects and stores data, often in a proprietary format unique to the data ecosystem. An example of a data ecosystem for analytical chemistry data is the EMPOWER™ ecosystem provided by Waters Corp. of Milford, Massachusetts.

The data ecosystem may include a library structure configured to deserialize the first model structure. Serialization may refer to the process of translating a data structure or object state into a format that can be stored or transmitted and reconstructed later. A library structure may be a shared library that provides capabilities shared across a computing platform, such as an operating system or data ecosystem. An example of a library structure is a dynamically-linked library (DLL).

A command signal may be received, where the command signal is configured to initiate a transfer of at least a part of the one or more results sets from the database to a cloud-based storage service. A cloud-based storage service may be a storage facility accessible via a network that provides data storage as a service. Cloud service providers are often associated with capabilities such as on-demand access to data and just-in-time capacity. An example of a cloud-based storage service is the SIMPLE STORAGE SERVICE (S3) provided by AMAZON WEB SERVICES (AWS).

An uploader may be called to transfer the part of the one or more results sets to the cloud-based storage service. The uploader may include a copy of the library structure of the data ecosystem.

The library structure may be used at the uploader to transform the part of the one or more results sets into a second model structure configured to be stored in a relational data store. For example, the results sets may be stored in a data warehouse of the cloud storage service. An example of a data warehouse is REDSHIFT provided by AWS. In order to transform the results sets into a format recognizable by the data warehouse, the system may make use of an extract, transform, load (ETL) service, such as AWS GLUE. The part of the one or more results sets may be stored with the cloud-based storage service according to the second model structure.

Because the library structure is incorporated directly into the uploader, it is not necessary to rely on the library structure built into the data ecosystem. Thus, when uploading the data, the uploader does not need to go through the data ecosystem. Instead, the uploader relies on its own copy of the library structure to deserialize the data. Thus, the uploader avoids the security, auditing, and other overhead of the data ecosystem, resulting in uploads that are much faster than if the uploader were to rely on interface calls into the data ecosystem.

Moreover, because the data is stored in a relational data store at the cloud-based storage service, it may be faster to access the data stored in the cloud service. Relational databases are generally optimized to perform data reads, and in this context the system will typically be performing a large number of reads from the database for a given piece of data. By using a relational database, data access can be optimized across the large amounts (e.g., many petabytes) of data that may need to be analyzed in an analytical chemistry experiment.

According to a second embodiment, the database may be provided on a legacy data storage device and the uploader may be provided on a separate uploader device. The separate uploader device may be configured to interface with the legacy data storage device to copy the database from a shared storage location. For example, the data from the legacy data storage device may be copied onto a portable drive, such as an AWS SNOW device, that is capable of interfacing with an uploader as described above. As data is retrieved from the legacy data storage (e.g., backups, tape drives, etc.), it can be quickly uploaded to the cloud storage service. This enables older data that might otherwise be lost or very difficult to use to be leveraged in analyses and visualizations. In this way, data quality can be improved because more data can be accessed in the cloud storage service.

According to a third embodiment, the database may be associated with one or more derived channels, and the uploader may use the library structure to generate information for the derived channels. A derived channel may be a channel defined in the data ecosystem. The derived channel may include data that is not directly collected during an experiment (or not directly collected in the form defined by the derived channel), but that is derived from collected data. In some cases, derived data may include data that was directly collected, but not organized in the way defined by the derived channel—one example would be when a photodiode array (PDA) detector measures multiple wavelengths of light, and the derived channel includes data collected for a first wavelength until a specified point in time, and then switches to a second wavelength. Derived data channels can be user-defined in the data ecosystem, which can make it difficult to predict what a derived data channel might look like for purposes of uploading the data. Because the uploader includes its own version of the library structure, the derived data that might otherwise only be accessible through the data ecosystem can be added to the cloud storage service.

According to a fourth embodiment, a security procedure may be performed in order to reduce or eliminate the need to rely on security processes of a data ecosystem. This may involve performing a handshake process between the uploader and the cloud-based storage service to download a certificate. The certificate may be linked to a tenancy on the cloud-based storage service, and the handshake may be performed prior to storing the part of the one or more results sets with the cloud-based storage service. The uploader may be authenticated with the cloud-based storage service using the certificate. The part of the one or more results sets may be isolated in the cloud-based storage service based on the tenancy associated with the certificate.

With this technique, the uploader can still be authenticated (and users individual data can be segregated and access-controlled within the cloud storage service) without the need to rely on the security procedures of the data ecosystem. This can further reduce the need to load unnecessary processes from the data ecosystem, further speeding up data uploading.

According to a fifth embodiment, the command signal may be received in response to a database trigger configured to be executed automatically when the one or more results sets are created or modified, or in response to a user instruction to upload a specified set of data from the one or more results sets. A database trigger may be procedural code that is automatically executed in response to certain events on a particular table or view in a database.

By establishing a database trigger that fires when results are created or modified, new or updated results can be automatically uploaded to the cloud storage service without the need to wait for manual intervention. This speeds up data uploading and improves the quality of data visualizations, since more recent data can be automatically leveraged.

As an alternative or in addition to using a trigger, exemplary embodiments may schedule the uploader to run as a scheduled batch process, configured to wake up on a regular basis (e.g., at predetermined intervals). Upon waking up, the uploader may upload any data that has been newly added or modified since the last upload.

According to a sixth embodiment, the database may store the one or more results sets in a materialized view. A materialized view may be a pre-computed data set derived from query specifications. When triggers are added directly to tables, as in the fifth embodiment, one issue that can arise is that the triggers create performance issues due to database locking and the need to constantly recompute data when executing database queries. By first creating a materialized view before performing the uploading, these performance issues can be avoided.

According to a seventh embodiment, a stored procedure within the database may be run in response to the command signal. The stored procedure may be configured to send an application programming interface (API) call to the uploader. The uploader may be configured to listen for the API call to initiate the transfer. Using a stored procedure to trigger the uploader provides a fast and automatic way to cause the uploader to initiate the data upload process.

Some embodiments pertain to creating visualizations for trending data. These embodiments may be performed separately or in conjunction with any of the embodiment described above. For example, the "data" and "datasets" referred to in connection with the trending data visualizations may refer to data that has been uploaded using the techniques described above in embodiments one through seven.

In an eighth embodiment, data associated with an analytical chemistry system may be received and automatically uploaded to a cloud-based storage service. A selection of a dataset may be received in a visualization interface, where the uploaded data is incorporated into the selected dataset. A configuration of a trending data setting for the dataset may be received, and a visualization of the dataset may be generated based on the trending data setting configuration. For example, the trending data setting may include a type of visualization (e.g., a type of graph, diagram, chart, or table) to be used to visualize the data, as well as settings (such as filters, reference lines, display settings, etc.) for the visualization. The visualization may be displayed in a visualization dashboard. By visualizing data that is automatically uploaded to the cloud-based storage service, trends across large amounts of data (that become available with automatic uploading and cloud storage) can be quickly identified and explored.

According to a ninth embodiment, the visualization may display one or more of: a method performance, a column performance, a product performance, a product stability, a system suitability, a site performance, a system performance, or an analyst performance. A method may refer to an analytical method used to analyze chemistry data. A column may be a column of an analytical laboratory instrument, such as a gas or liquid chromatograph. Product performance and stability may refer to the potency, quality, strength, and/or stability (e.g., degradation in performance over time) of given analyte or compound. System suitability may refer to the suitability of one or more configured analytical laboratory instruments for achieving the types of measurements required by an analytical chemistry experiment. Site performance may refer to the performance of a group of instruments at a given location (such as an analytical laboratory). System performance may refer to the performance of one or a selected group of laboratory analytical instruments (e.g., as measured through the repeatability of results, how well the instruments measure known standards, maintenance schedules, etc.). Analyst performance may describe the accuracy or efficiency of a particular user, potentially across multiple different instruments.

These options allow users to monitor the performance of labs, equipment, users, etc. on an ongoing basis. The system may be configured to generate a visualization of these aspects on a regular basis dependent on the type of data being visualized (e.g., daily, weekly, monthly, quarterly, yearly, multi-year, etc.).

According to a tenth embodiment, the dataset may be a first dataset associated with a first analytical chemistry project. A selection of a second dataset from a second analytical chemistry project may be received in the visualization interface. The first dataset and the second dataset may be combined to create a combined dataset, and a visualization of the combined dataset may be generated. In this way, trends can be analyzed across multiple different datasets, potentially created at different times.

According to an eleventh embodiment, the visualization dashboard may be connected to the dataset. When new data is received in the dataset, the visualization may be automatically updated with the new data. Accordingly, visualization dashboards can be displayed in an interface that allow users to quickly access the most up-to-date cloud data and identify trends in the data more rapidly.

According to a twelfth embodiment, an interactive control element may be displayed in the visualization interface, where the interactive control element is associated with a predefined configuration of settings or filters. A selection of the interactive control element may be received, and the visualization may be updated based on the predefined configuration. Such a control element allows a user to quickly apply preset configurations that may be well-suited to visualizing certain types of data. It also allows visualizations to be created more efficiently because users need to regenerate visualization configurations with many of the same settings for similar types of data.

According to a thirteenth embodiment, the visualization may include a plot made up of a plurality of data points. A selection of one of the plurality of data points may be received, and a chromatogram associated with the selected data point may be retrieved in response. The retrieved chromatogram may be displayed in the visualization dashboard. This allows the user to drill down into individual results, which can allow them to more quickly identify outliers and/or see how a particular dataset contributed to a data trend.

According to a fourteenth embodiment, the dataset may be a first dataset. A selection of a second dataset may be received, and the second dataset may be overlaid on the first dataset in the visualization interface. This allows for trends to be identified between different datasets.

Unless otherwise noted, it is contemplated that each embodiment may be used separately to achieve the advantages specifically identified above. It is also contemplated that the embodiments described above (and elsewhere herein) may be used in any combination to achieve further synergistic effects. Other technical features will be readily apparent to one skilled in the art from the following figures, descriptions, and claims.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
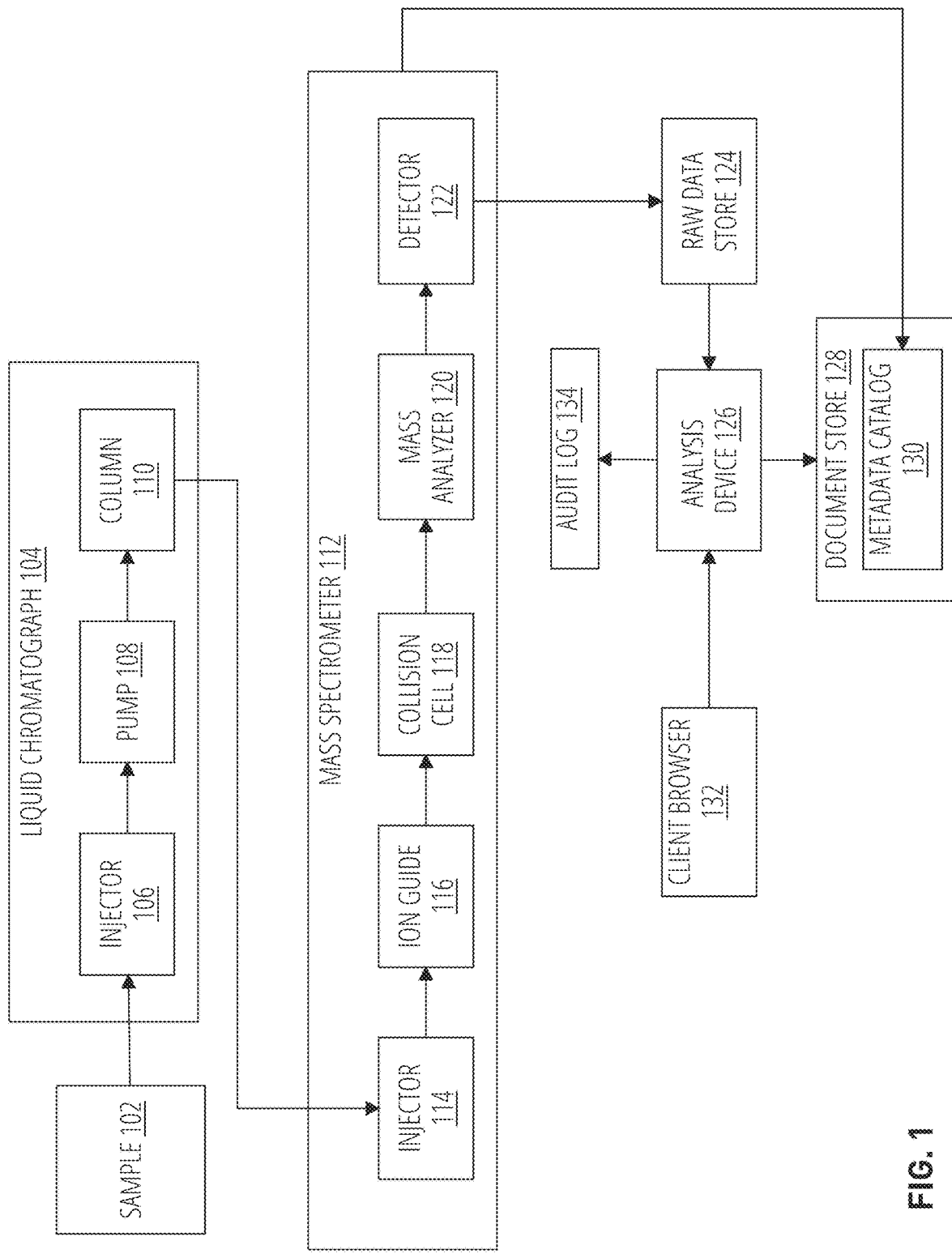
FIG. 1 illustrates an example of a mass spectrometry system according to an exemplary embodiment.

As an aid to understanding, a series of examples will first be presented before detailed descriptions of the underlying implementations are described. It is noted that these examples are intended to be illustrative only and that the present invention is not limited to the embodiments shown.

Reference is now made to the drawings, wherein like reference numerals are used to refer to like elements throughout. In the following description, for purposes of explanation, numerous specific details are set forth in order to provide a thorough understanding thereof. However, the novel embodiments can be practiced without these specific details. In other instances, well known structures and devices are shown in block diagram form in order to facilitate a description thereof. The intention is to cover all modifications, equivalents, and alternatives consistent with the claimed subject matter.

In the Figures and the accompanying description, the designations "a" and "b" and "c" (and similar designators) are intended to be variables representing any positive integer. Thus, for example, if an implementation sets a value for a=5, then a complete set of components 122 illustrated as components 122-1 through 122-a may include components 122-1, 122-2, 122-3, 122-4, and 122-5. The embodiments are not limited in this context.

These and other features will be described in more detail below with reference to the accompanying figures.

For purposes of illustration, FIG. 1 is a schematic diagram of an analytic chemistry system that may be used in connection with techniques herein. Although FIG. 1 depicts particular types of devices in a specific liquid chromatography/mass spectrometry (LCMS) configuration, one of ordinary skill in the art will understand that different types of chromatographic devices (e.g., MS, tandem MS, etc.) may also be used in connection with the present disclosure.

A sample 102 is injected into a liquid chromatograph 104 through an injector 106. A pump 108 pumps the sample through a column 110 to separate the mixture into component parts according to retention time through the column.

The output from the column is input to a mass spectrometer 112 for analysis. Initially, the sample is dissolved and ionized by a desolvation/ionization device 114. Desolvation can be any technique for desolvation, including, for example, a heater, a gas, a heater in combination with a gas or other desolvation technique. Ionization can be by any ionization techniques, including for example, electrospray ionization (ESI), atmospheric pressure chemical ionization (APCI), matrix assisted laser desorption (MALDI) or other ionization technique. Ions resulting from the ionization are fed to a collision cell 118 by a voltage gradient being applied to an ion guide 116. Collision cell 118 can be used to pass the ions (low-energy) or to fragment the ions (high-energy).

Different techniques may be used in which an alternating voltage can be applied across the collision cell 118 to cause fragmentation. Spectra are collected for the precursors at low-energy (no collisions) and fragments at high-energy (results of collisions).

The output of collision cell 118 is input to a mass analyzer 120. Mass analyzer 120 can be any mass analyzer, including quadrupole, time-of-flight (TOF), ion trap, magnetic sector mass analyzers as well as combinations thereof. A detector 122 detects ions emanating from mass analyzer 122. Detector 122 can be integral with mass analyzer 120. For example, in the case of a TOF mass analyzer, detector 122 can be a microchannel plate detector that counts intensity of ions, i.e., counts numbers of ions impinging it.

A raw data store 124 may provide permanent storage for storing the ion counts for analysis. For example, raw data store 124 can be an internal or external computer data storage device such as a disk, flash-based storage, and the like. An analysis 126 analyzes the stored data. Data can also be analyzed in real time without requiring storage in a storage medium 124. In real time analysis, detector 122 passes data to be analyzed directly to analysis 126 without first storing it to permanent storage.

Collision cell 118 performs fragmentation of the precursor ions. Fragmentation can be used to determine the primary sequence of a peptide and subsequently lead to the identity of the originating protein. Collision cell 118 includes a gas such as helium, argon, nitrogen, air, or methane. When a charged precursor interacts with gas atoms, the resulting collisions can fragment the precursor by breaking it up into resulting fragment ions. Such fragmentation can be accomplished by switching the voltage in a collision cell between a low voltage state (e.g., low energy, <5 V) and a high voltage state (e.g., high or elevated energy, >15V). High and low voltage may be referred to as high and low energy, since a high or low voltage respectively is used to impart kinetic energy to an ion.

Various protocols can be used to determine when and how to switch the voltage for such an MS/MS acquisition. After data acquisition, the resulting spectra can be extracted from the raw data store 124 and displayed and processed by post-acquisition algorithms in the analysis 126.

Metadata describing various parameters related to data acquisition may be generated alongside the raw data. This information may include a configuration of the liquid chromatograph 104 or mass spectrometer 112 (or other chromatography apparatus that acquires the data), which may define a data type. An identifier (e.g., a key) for a codec that is configured to decode the data may also be stored as part of the metadata and/or with the raw data. The metadata may be stored in a metadata catalog 130 in a document store 128.

The analysis 126 may operate according to a workflow, providing visualizations of data to an analyst at each of the workflow steps and allowing the analyst to generate output data by performing processing specific to the workflow step. The workflow may be generated and retrieved via a client browser 132. As the analysis 126 performs the steps of the workflow, it may read raw data from a stream of data located in the raw data store 124. As the analysis 126 performs the steps of the workflow, it may generate processed data that is stored in a metadata catalog 130 in a document store 128; alternatively or in addition, the processed data may be stored in a different location specified by a user of the analysis 126. It may also generate audit records that may be stored in an audit log 134.

Figure 12:
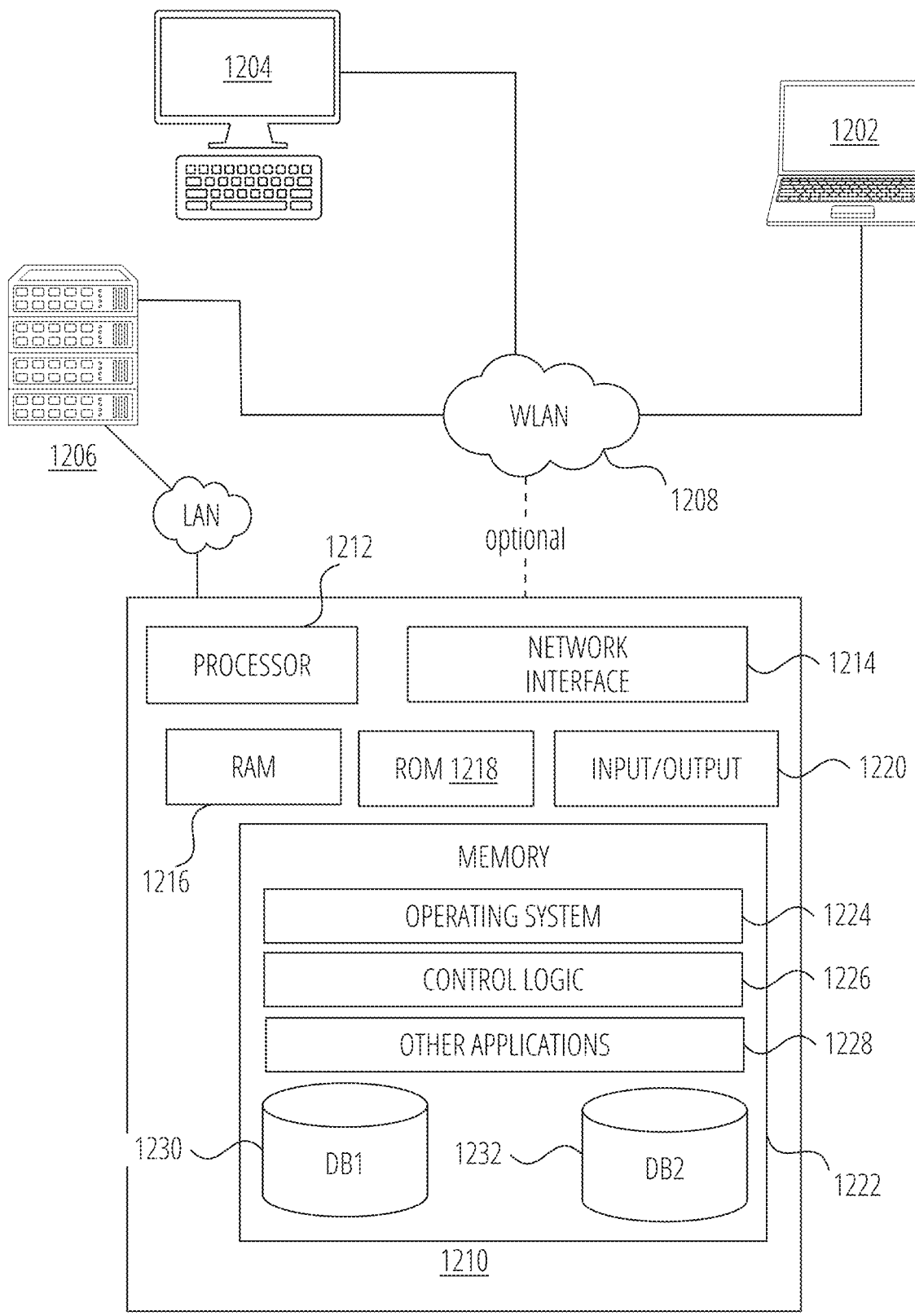
FIG. 12 depicts an illustrative computer system architecture that may be used to practice exemplary embodiments described herein.

The exemplary embodiments described herein may be performed at the client browser 132 and analysis 126, among other locations. An example of a device suitable for use as an analysis 126 and/or client browser 132, as well as various data storage devices, is depicted in FIG. 12.

Figure 2A:
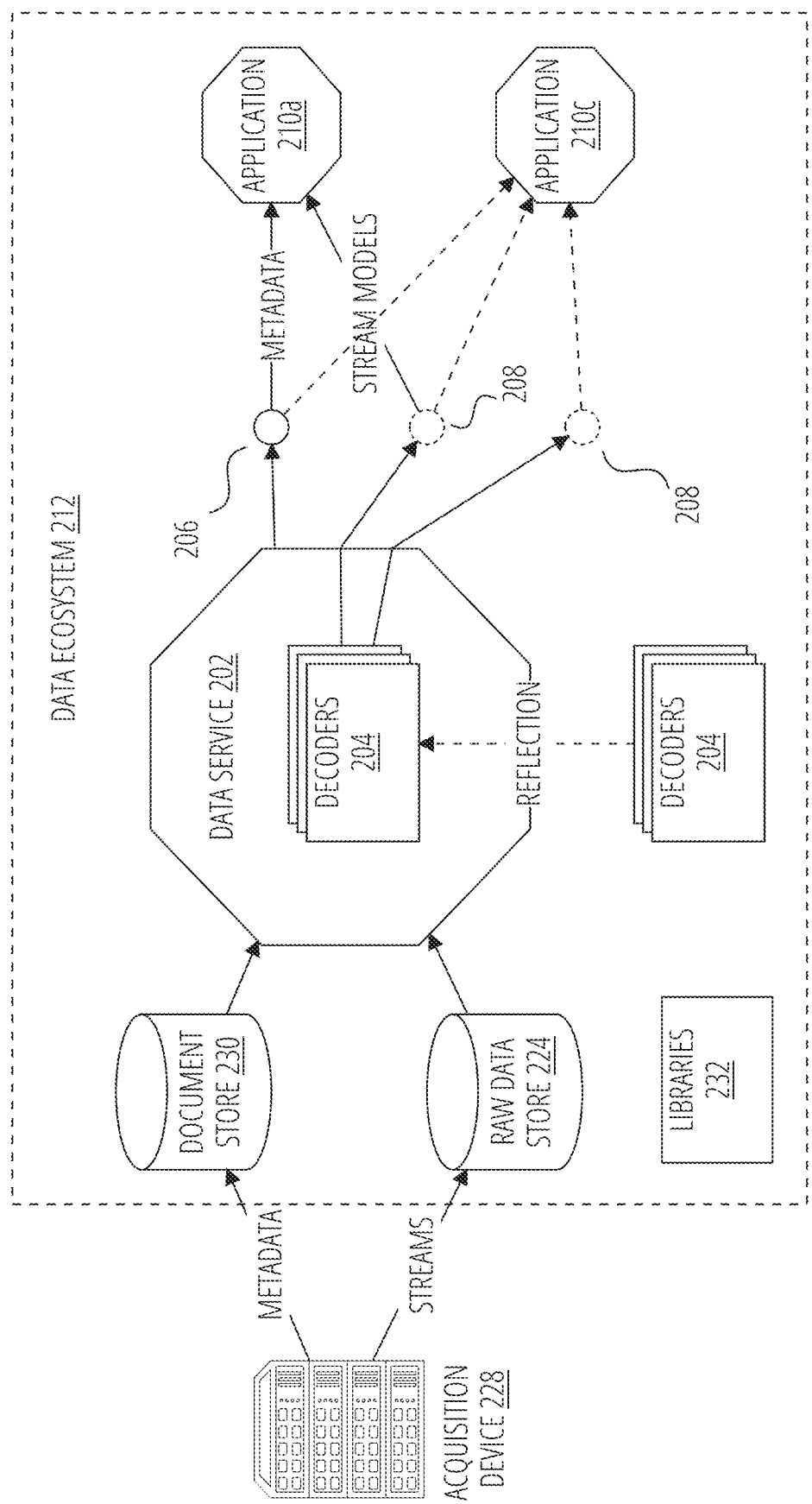
FIG. 2A illustrates a first exemplary data processing ecosystem in accordance with one embodiment.

FIG. 2A depicts an exemplary data ecosystem 212 for storing and retrieving chromatography data.

A chromatography acquisition 228, such as a spectrometer, chromatography, or other device, may perform and output measurements (e.g., as a stream of readings formatted according to a data type that is specific to the acquisition 228 and/or settings applied to the acquisition 228). Those measurements may be stored in a raw data store 224.

In one example, the acquisition 228 may acquire samples using an acquisition controller service. The acquisition controller service may submit the samples, via a RESTful API call, to an acquired data receiver autonomous service. The acquired data receiver autonomous service may create a sample set, which represents the multiple samples sent for analysis into an instrument. In other words, a sample set is an organized sequence of several injections that were sent into the chromatography apparatus.

The raw data raw data store 224 may include data from multiple different chromatography apparatuses and/or chromatography apparatuses operating in multiple different acquisition modes. Accordingly, the data processing environment acts as a single source of data for applications, regardless of which device generated the data (or which mode the data was operating in). Any application calling into the ecosystem can be sure that any acquired data can be accessed and processed appropriately.

The sample set may be stored in a sample set model store, while injection raw data blobs may be sent to a separate acquired data raw blob store. The data may generally be stored in an oracle database as one or more models, which may represent a serialized format for storing the data. The serialized format may be a proprietary format. The models can be streamed to various applications and/or requested via interface calls. One or more libraries 232 built into the data ecosystem 212 may be capable of reading the models and deserializing them by converting them into basic modules. The libraries 232 may be, for example, dynamically linked libraries (DLLs) for the data ecosystem 212. In addition to deserializing the models, the libraries 232 may also describe derived channels in the data by defining how to transform measured data into a different type, format, or organization of data.

The acquisition 228 may also generate metadata describing the configuration of the acquisition 228, details of the experiment being performed, a decoder configured to decode data generated for the experiment, etc. This metadata may be stored in a metadata catalog 130. As with the raw data store 224, the metadata catalog 130 may store metadata associated with multiple different acquisition devices in multiple different configurations.

The raw data may be decodable by a set of decoders 204, where each decoder is associated with a particular data type. For example, the decoder may be associated with a particular type of raw data generated by a chromatography instrument in a specific acquisition mode. That instrument may output a stream of raw data, including (e.g.) binary data, arrays of information, etc. The decoder may be programmed to parse a stream of raw data generated by such an instrument so that the data stream can be meaningfully interpreted.

In some embodiments, a single decoder may be associated with multiple data types; in further embodiments, multiple versions of the same decoder may each be associated with different data types. The decoders 204 may be embedded within a data service 202, such as an autonomous service (e.g., via reflection).

Each of the autonomous services may expose one or more endpoint interfaces. A particular decoder may be associated with each endpoint interface. The decoder may be configured to interpret the raw data that is associated with the endpoint interface.

For example, these endpoints may be Representation State Transfer (REST) endpoints capable of receiving RESTful Application Programming Interface (API) calls. An endpoint interface may receive a request for raw data acquired by a chromatography instrument. The data ecosystem 218 may expose multiple endpoint interfaces; for example, each autonomous service may be associated with and may expose at least one endpoint interface. An application 210a, 310c configured to process the raw data may call into the endpoint interface using an API call in order to retrieve the data.

The autonomous service (or another construct) may retrieve the requested raw data from a raw data store, apply the decoder to the raw data to generate decoded data, and may return the decoded data in response to the original request. For example, the autonomous service may apply the decoder to the raw data and provide decoded data to the requesting application, or the autonomous service may identify the decoder and provide it (or a location at which it can be accessed) to the requesting application along with the raw data (or a location of the raw data). In the latter case, the application may decode the data with the decoder.

Returning to the above-described example, the autonomous service may retrieve the sample set models from the sample set model store and/or may retrieve the raw data blobs from the raw data blob store. The data may be decoded according to the decoder, and either version of the data (the raw data blobs or the sample set) may be provided to the application. The reason for supplying either or both of the raw data blobs and the sample set models is that the application may be tuned, for performance reasons, to use one or the other representation of the data.

By exposing the endpoint interfaces in this way, an application 210a, 310c can request data acquired by a chromatography instrument without needing to understand how to interpret the data. Furthermore, an application 210a, 210c may deposit the data in a known or common format into a central repository along with metadata indicating, e.g., when the data was received by the application, when the data was processed by the decoder, the identity of user who captured the data, the identity of the instrument that generated the data, and other information describing how and when the data was acquired. Accordingly, when new types of instruments are brought online (potentially outputting data in a different streaming format), it is not necessary to reprogram each application 210a, 310c that might use that data. Because each application 210a, 210c need not be programmed with specifics of how to interpret each different type of data stream, more different types of data can be made available to the applications, which allows for more complex analyses. This configuration also allows multiple different types of data to be stored together in a common source structure, simplifying data retrieval and storage.

In the depicted embodiment, the endpoint interfaces are of two types. A first type serves as a catalog endpoint 206, which is configured to receive requests for metadata. In response to receiving a request for metadata on the catalog endpoint 206, the data service 202 may identify the corresponding metadata in the metadata catalog 130. The data service 202 may then either return the requested metadata to the requesting application or may return the location of the metadata so that it can be retrieved by the application as needed.

Another type of endpoint interface may serve as a data endpoint 208. There are generally a number of data endpoints 208 in the data ecosystem 212 corresponding to a number of data types that the raw data store 224 is capable of supporting. Each data endpoint 208 is characterized by a data type. When an application requests data, it may call into the raw data store or the metadata catalog to identify the type of the data; for example, the data may be tagged with a codec key that is stored with the data and/or in the metadata. The endpoint interfaces may be callable based on the data type, so once the data type is known the requesting application may identify the appropriate endpoint interface to decode the data and may formulate an appropriate RESTful API call to communicate with the interface. This provides an efficient way for the application to identify and call into the autonomous service that is capable of decoding the data.

Consequently, incoming requests are separated into metadata-specific requests and data-specific requests. Each is handled by a different type of endpoint. This helps to segregate incoming requests and provides requesting applications with a known endpoint to target for appropriate types of requests.

In this example, a single autonomous service handles requests for metadata and each different data type. Although straightforward to implement, it may be necessary to update the entire autonomous service every time one of the data types is changed, or a new data type is added. This can cause unnecessary downtime. Furthermore, the autonomous service needs to be capable of accessing both the metadata catalog 130 and the raw data store 224. These issues can be alleviated by dividing responsibility for different tasks between different autonomous services. An example of such an environment is described next in connection with FIG. 2B.

Figure 2B:
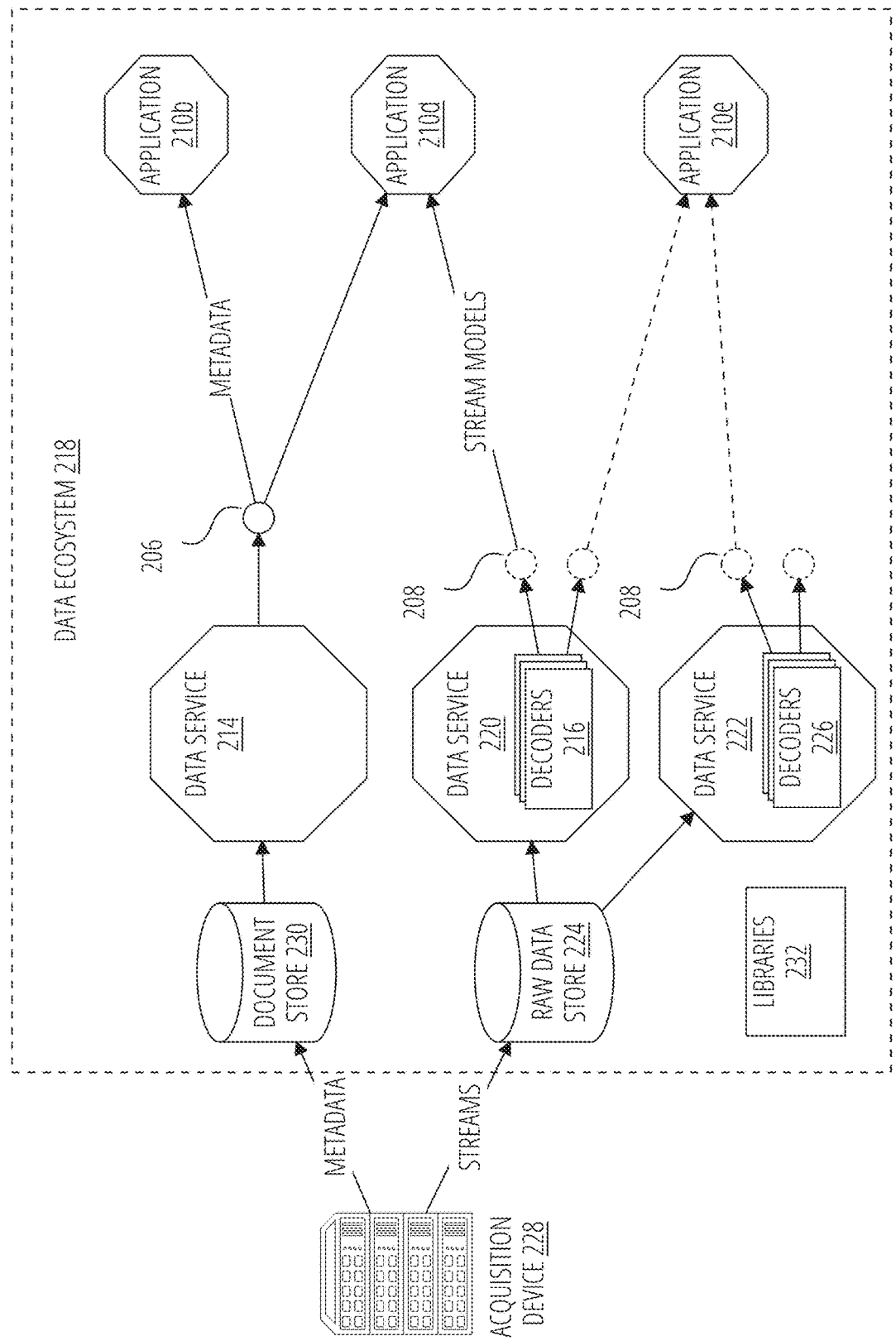
FIG. 2B illustrates a second exemplary data processing ecosystem in accordance with another embodiment.

FIG. 2B illustrates an alternative configuration in which (1) metadata requests are all directed to a particular data service 214, which interfaces with the document store 230 but not the raw data store 224, and (2) data requests are submitted to any of a number of additional autonomous services, each of which has a particular decoder or set of decoders embedded and handles requests specific to the data type of its embedded decoders.

In this configuration, multiple data services 220, 322, etc. service incoming requests for data. Furthermore, at least one data service 214 is specifically configured to respond to requests for metadata. The data service 214 responding to metadata requests does not respond to requests for data, and accordingly does not need to implement any functionality related to the decoders. Similarly, the data services 220, 322, etc. responding to data requests do not need to implement any of the functionality for querying the metadata catalog. When new data types are added, a new autonomous service implementing the decoder for the new data type may be added, or an existing autonomous service may be updated with the new functionality. Meanwhile, most of the autonomous services can remain unchanged. Similarly, if the metadata catalog API is ever changed, only the metadata-handling autonomous service needs to be updated.

The raw data raw data store 224 includes data of multiple different data types. Collectively, the autonomous services may be configured to decode each of the plurality of different data types. For example, the multiple different data types may be included in an interface specification, which may describe how to decode the various different types. The interface specification may be capable of being implemented, at least in part, by each of the autonomous services by implementing corresponding data endpoints 208 and decoders 216, 324. Each data service 220, 322 may be associated with a different set of decoders 216, 324, although there may be some overlap in the decoders supported by different data services. However, no single data service implements all of the decoders, so the functionality for decoding different types of data is distributed across multiple data services. Therefore, different parts of the interface specification may be split between multiple different autonomous services, so that each implements a part, but not all, of the interface specification. Each part of the interface specification may be implemented by at least one of the autonomous services so that, collectively, the group of interface services implements the interface specification.

Because each autonomous service is tasked with only implementing a portion of the interface specification, each autonomous service can be made simpler (since it need not be concerned with providing decoders and endpoint interfaces for portions of the interface specification that it does not implement). New autonomous services can be easily added to deal with new capabilities, and it is not necessary to take down all of the autonomous services when one decoder needs to be updated.

Figure 3:
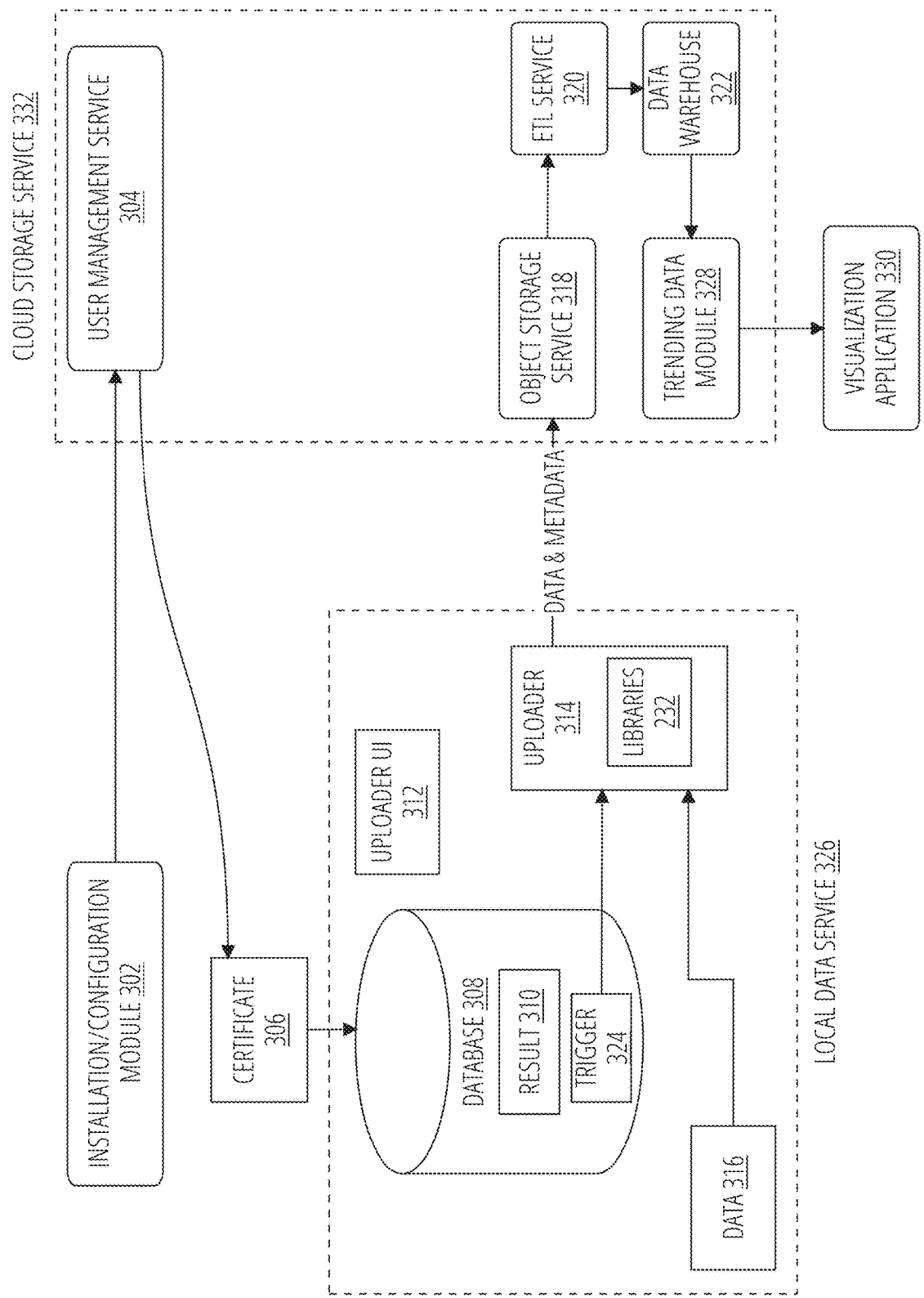
FIG. 3 illustrates an environment with an uploader and cloud storage service in accordance with one embodiment.

FIG. 3 depicts an exemplary environment including an uploader 314 and a cloud storage service 332. The uploader 314 may be configured to upload data stored in a local data service 326, such as a database system. An example of a local data service 326 is the ORACLE DATABASE MANAGEMENT SYSTEM (DBMS).

The environment includes an installation/configuration module 302 for the uploader. The installation/configuration module 302 may include a setup file that installs the uploader 314 on a computing device. As part of the installation of the uploader 314, the installation/configuration module 302 may perform a handshaking process with the cloud storage service 332 that authenticates the uploader 314 with the cloud storage service 332. To that end, the installation/configuration module 302 may communicate with a user management service 304 of the cloud storage service 332 to authenticate the user, organization, or other entity installing the uploader 314. An example of a user management service 304 is the COGNITO service provided by AWS, which registers users with the cloud storage service 332, establishes tenancies, and maintains and enforces access rights.

Once authenticated, the installation/configuration module 302 may install the uploader 314 on the computing device. The user management service 304 may provide a certificate 306 evidencing the authentication, which may be installed with the uploader 314 on the computing device. When uploading data, the uploader 314 may use the certificate 306 to authenticate itself to the cloud storage service 332.

Data stored in the database 308 of the local data service 326 may be organized into projects. Each project may represent a user-configurable collection of data sets. The data sets may be updated as new results are received from experiments. The uploader 314 may upload all data in a project (referred to as "seeding") or may upload data related to particular results as they are received (referred to as a real-time trickle).

The uploader 314 may include an uploader UI 312 allowing the user to select data to be manually seeded into the data warehouse 322. In order to upload data in the real-time trickle, the database 308 may be configured with one or more database triggers 324. The triggers 324 may be configured to fire when new data is added to the database 308. Each trigger 324 may be associated with a stored procedure within the database 308, where the stored procedure sends an API call (such as a REST call) to the uploader 314. The uploader 314 may be configured to listen for the REST call and begin uploading the data that triggered the call to the cloud storage service 332.

In order to facilitate queries, the database 308 may store the data in a materialized view. The materialized view may be precomputed based on the form of queries used by the local data service 326.

A goal of the uploader may be to transfer at least some of the data stored in the database 308 into a data warehouse 322. Because the data warehouse 322 will likely respond to many queries for the data, the 322 may store the data in a form that is optimized for read access. For instance, the data warehouse 322 may be a relational database such as AWS REDSHIFT.

The data warehouse 322 may need to store the data in a particular form in order to optimize for read access. This may differ from the form used to store the data in the database 308. Thus, the uploader 314, in conjunction with an object storage service 318 and an ETL service 320, may transform the data from a first data model used to store the data in the database 308 to a second data model used to store the data in the data warehouse 322.

To that end, the data may be uploaded to an object storage service 318 of the cloud storage service 332, such as AWS S3. The object storage service 318 may by a multi-tenant storage service that stores data in tenant-specific buckets. During installation, the installation/configuration module 302 may prompt the user to enter a tenancy ID or name that represents the user in the user management service 304. The tenancy ID/name may be stored in the local data service 326 so that the uploader 314 can isolate a specific user's data in a user-specific bucket of the object storage service 318.

In addition to the raw data, derived data and metadata may also be uploaded to the object storage service 318. The metadata may include, for example, a tenancy identifier that identifies a tenancy associated with a user of the uploader in the cloud storage service 332. Furthermore, the metadata may include a project identifier that indicates a project that the uploaded data belongs to. Still further, the metadata may include a channel identifier for stream files uploaded by the uploader. Other information may also be included in the metadata, such as sample set and result set information, historical instrument state changes throughout the acquisition process, and instrument diagnostic telemetry such as pump pressures, lamp run time, oven temperatures, column Etag counts, etc.

The ETL service 320 may be configured to watch for new data entering the object storage service 318 (e.g., using a serverless compute service, such as AWS LAMBDA), transform it (e.g., into the second data model), and store the transformed data in the data warehouse 322.

A trending data module 328 may access data stored in the data warehouse 322 and analyze it to identify data trends. The trending data module 328 may include artificial intelligence or machine learning (AI/ML) capabilities to identify the data and suggest the best way to visualize it. An example of a trending data module 328 suitable for use with exemplary embodiments is AWS QUICKSIGHT.

The trending data module 328 may identify commonly requested configurations and select the most appropriate visualizations for them. For example, the trending data module 328 may identify that available data contains a set of fields that can be used to perform a particular type of analysis. Alternatively or in addition, a user may select a set of fields and the trending data module 328 may recognize that the selected fields commonly correspond to a particular type of analysis or visualization.

Examples of types of analyses that may be recognized by the trending data module 328 include: method performance, column performance, product performance, product stability, system suitability, site performance, system performance, system flexibility, system usage, and analyst performance.

Method performance analysis may be used to determine if a current method (e.g., a United States Pharmacopeia, or "USP," method) can be improved. For example, the system may review existing separation parameters for a given component in a sample, and determine if a set of performance criteria are met. If not, the method may be flagged for improvement—for example, portions of the visualization graph(s) where the criteria are not met may be highlighted or shown in a different color. One example of the above-described performance criteria are:

when the Retention (K') value falls in a particular range: $1.0 \leq K' \leq 20.0$ Resolution (Rs) Between an Active Pharmaceutical Ingredient (API) and Related Substance: >2.00, all other peaks >2.00, no individual peak <1.50

USP tailing (T) For all identified peaks: >1.50

In order to analyze method performance, the following trending data fields may be tracked: the name; identifier of the component or peak being considered, any specific projects within the data that are flagged for analysis, capacity factor, USP Tailing, and/or USP resolution. Method performance may be displayed in a visualization that depicts USP tailing versus run number, USP resolution versus run number, and/or capacity factor versus run number.

Column performance may encompass a number of aspects of a chromatography column; for example, column performance may measure column efficiency and chromatographic peak shape distortions such as peak tailing. The efficiency may be measured, for example, using the USP Plate Count versus run number for a specified peak for a specified number of projects. Peak tailing may be monitored by examining a specified peak (versus run number) for deformation. Both the efficiency and tailing may be visualized versus the run number for the specified number of projects.

The following trending data fields may be used to monitor column performance: the component or peak name, the specific projects to be compared, the USP plate count (tang), and/or the USP tailing. The corresponding visualization may graph the USP plate count versus the run number and/or the USP tailing versus the run number.

Product performance may measure, for example, the purity of a compound, active ingredient, or component (e.g., for products produced at a particular manufacturing site).

For example, consider the case where a product is manufactured at a manufacturing site, where the product has an active ingredient that is supposed to be present in a certain amount (referred to as the label claim). An analyst may perform analytical tests on each batch received into a laboratory from the manufacturing site. The tests may include identification of the product components, assaying the product, and determining impurities in the product. Given this information, the analyst may wish to determine what percent of each batch meet their label claims over a given time period (e.g., 1 year, 3 year, 5 years, 10 years).

To track purity, trending data fields including a component or peak name, specific project identifiers, and a percent label claim (which may be in a custom field) may be identified and visualized. The visualization may cover various time periods (e.g., 1 year, 3 years, 5 years, 10 years, etc.).

In a similar scenario, an analyst may wish to track product stability (which may track product performance over a given timeframe). For example, the analyst may perform identification, assay, and impurities tests on the products, and the percent label claim achieved may be measured as above. For accelerated stability products, the same information may be calculated at shorter durations (e.g., 0, 1, 3, and 6 months). For real-time studies, this information may be determined at 0, 6, and 12 months, and then once a year thereafter (although these time periods will vary depending on the product and testing to be done). For products stored in blister packs, these values may be calculated over time for storage at different temperatures (e.g., 4° C., 25° C., 30° C., 40° C., etc.). They may also be calculated for different sizes of blister packs (e.g., 100, 300, 500, and bulk-sized packs).

To track product stability, the data fields tracked may include the component or peak name, specific key projects, the temperature and/or relative humidity at which the product was stored, the percent label claim, time points for when the product was initially stored and/or for when testing occurred, named impurities (% recovered), and/or unknown impurities (% recovered).

System suitability may indicate how well a given device in a given configuration can detect a desired component in a sample. For a given component or peak name, the system may determine, from a certain number of injections (e.g., 6), the percent relative standard deviation (% RSD) for retention time and the % RSD for area and height. These % RSD values should be less than or equal to a certain minimum threshold (e.g., 2%) as determined for the particular column used. The minimum resolution between two peaks should also be less than or equal to a specified minimum value (e.g., 1.5). This data may be visualized, for example, daily prior to each run, and weekly for a longer-term review.

Fields that may be tracked to measure system suitability include the component or peak name to be tracked, specific key projects, the retention time, and area, height, and resolution of the peaks.

Site performance may measure the efficiency and/or validity of a lab's analyses. Site performance may consider the types of tests performed (e.g., identification, assay, impurities, etc.). The time (e.g., in days) needed to run the tests (as measured based on the data the acquisition was performed to the date processed, between analyst sign-offs) may be computed and compared across different sites.

To measure site performance, the following fields may be tracked: component or peak name, specific key projects, the % label claim (which may be stored in a custom field), the site location (which may be stored in a custom field), the date on which the data was acquired, the date on which the acquiring analyst signed off on the acquisition, the date on which the data was processed, and/or the date the processing analyst signed off on the processing.

System performance may similarly be measured. System performance may measure a number of different metrics, such as: the number of samples acquired per day; the system usage over a given period as a percentage of injection time available in a 24-hour, 7-day week); which systems at a site have the highest and lowest usage; a system usage pattern for all systems organized by time of day and/or day of week. In the latter example, the visualization might indicate (eg., by color) differences between high and low usage times.

Fields that may be tracked to determine system performance may include the sample set identifier, the system name, the location of the system (potentially stored in a custom field), and the date(s) on which the system acquired sample sets.

System flexibility may be used to show the systems which have the highest number of available instrument methods, as compared to the lowest number, or the highest and lowest number of users. To track system flexibility, the following fields may be tracked: the system name, the number of channels on the system, the number of instrument methods on the system, and the number of users of the system.

Furthermore, the daily or weekly usage of a system may be monitored by tracking data such as the system name, date(s) on which the system was used for an acquisition, and/or the sum number of systems used over the time frame to be analyzed.

Analyst performance on a specific system, across systems, or across sites may also be tracked. The system may, for example, compare the assay (% label claim) results of two different analysts using the same system, solvents, and batch of product, potentially on different days. To track analyst performance, the system may monitor field including the component or peak name, the batch number, an identifier for a first analyst analyzing the product, an identifier for a second analyst analyzing the product, the % label claim (which may be stored in a custom field), specified projects, and the identifier or name of the system used to perform the analysis.

A method may refer to an analytical method used to analyze chemistry data. The trending data module 328 may recognize that a method is being analyzed when the available fields in the data set include fields that identify a method or method steps, or that quantify the performance of the method (e.g., by measuring the accuracy of the method against a known standard or by comparing the settings or parameters of the standard to a known best configuration).

A column may be a column of an analytical laboratory instrument, such as a gas or liquid chromatograph. Column performance may be measured by evaluating the repeatability of column measurements, or by determining how accurate the column readings are when compared to a known standard. The trending data module 328 may determine that column performance is being analyzed when the fields in the data set include an identifier of a column used to make the measurements and/or parameters commonly used to judge column performance (such as column age, a most recent calibration time, etc.).

Product performance and stability may refer to the potency, quality, strength, and/or stability (e.g., degradation in performance over time) of given analyte or compound. The trending data module 328 may determine that product performance or stability are being measured when the fields of the data set include an identifier of the product being considered, and/or measurements of the product's concentration, quality as compared to a reference product (such as a pure sample of the product), amount of impurities, etc., especially (in the case of stability) when these values are measured over a period of time.

System suitability may refer to the suitability of one or more configured analytical laboratory instruments for achieving the types of measurements required by an analytical chemistry experiment. The trending data module 328 may determine that system suitability is being measured when the fields of the data set include typical measurements of system suitability, such as an identifier for the system being analyzed, values for the configuration of the system, identifiers for the types of products that the system is configured to analyze, and/or measures of performance or the quality of results generated by the system.

Site performance may refer to the performance of a group of instruments at a given location (such as an analytical laboratory). System performance may refer to the performance of one or a selected group of laboratory analytical instruments (e.g., as measured through the repeatability of results, how well the instruments measure known standards, maintenance schedules, etc.). The trending data module 328 may determine that site performance is being analyzed when the fields of the data set include an identifier that associates particular instruments with a site (such as a laboratory identifier), especially if multiple instruments in the data set are associated with a particular site.

Analyst performance may describe the accuracy or efficiency of a particular user, potentially across multiple different instruments. The trending data module 328 may determine that analyst performance is being analyzed when the fields of the data set include an identifier for the analyst who generated the results, as well as measurements of the quality of the results generated by the analyst.

Based on the type of analysis being performed, the trending data module 328 may select an appropriate type of visualization (e.g., a chart, a particular type of graph such as a line graph or bar graph, a table, etc.). The type of visualization may be selected, at least in part, based on the dimensionality of the data. For example, if the selected fields represent a single data point, the value of the data point may be displayed in the visualization. If the data is two-dimensional, then a line graph may be an appropriate type of visualization.

The visualizations computed by the trending data module 328 may be presented in a visualization interface of a visualization application 330. The visualization application 330 may be an application running on a client device or in a browser and may be configured to display interfaces such as those depicted in FIG. 5-FIG. 9G.

Figure 4:
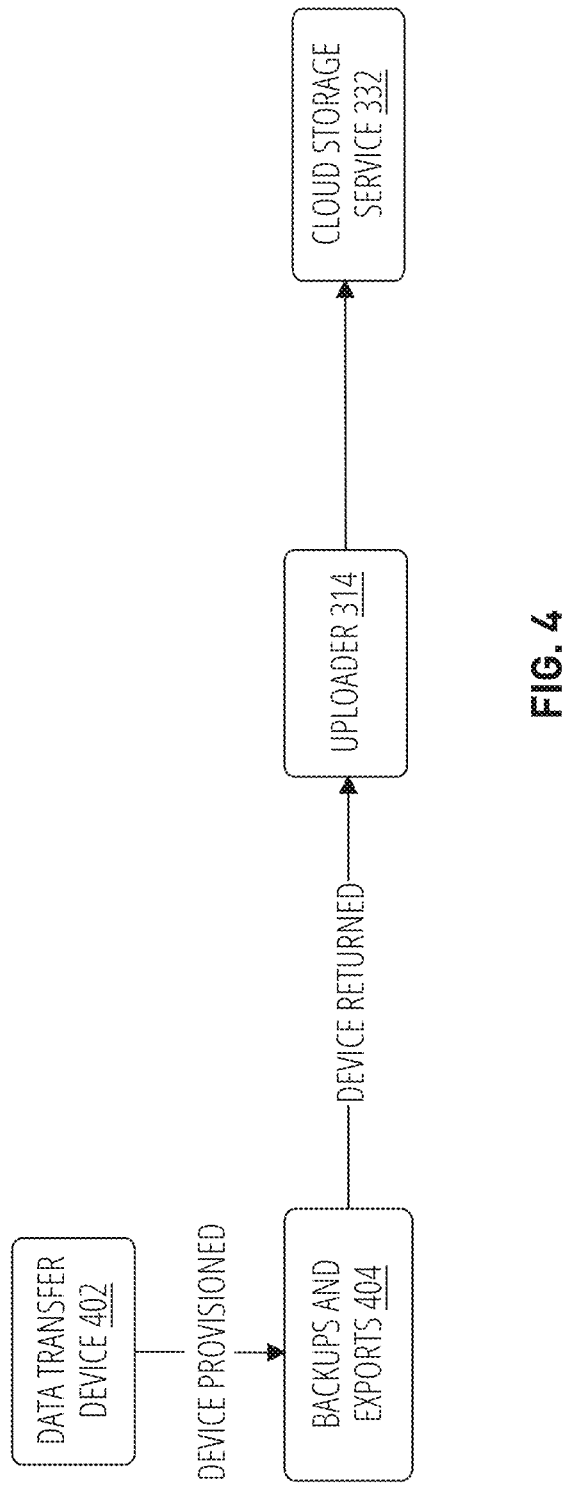
FIG. 4 illustrates a technique for uploading data from backups and exports in accordance with one embodiment.
Figure 5:
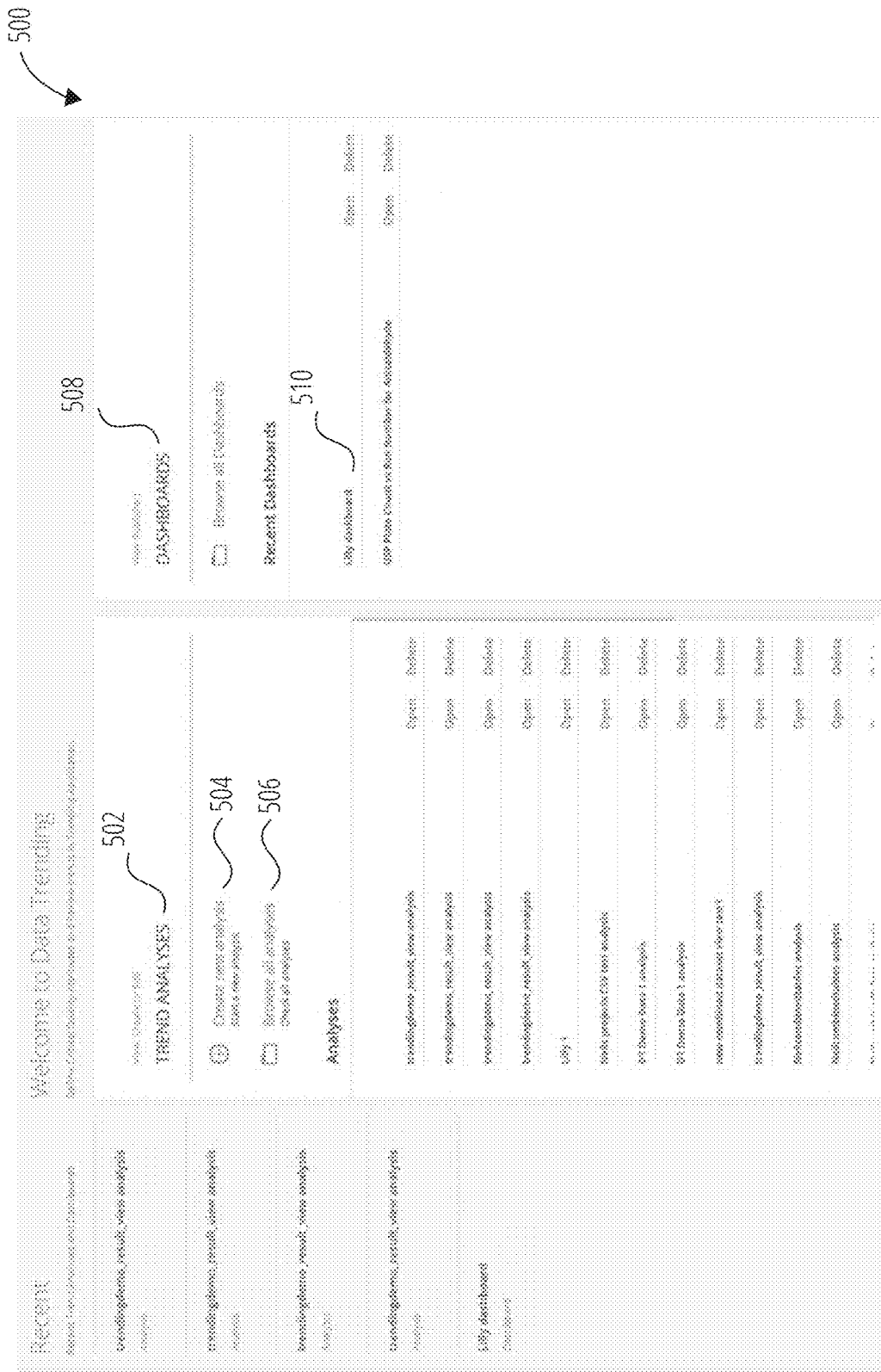
FIG. 5 illustrates an interface for a trending data application in accordance with one embodiment.

The embodiment depicted in FIG. 3 is well-suited to uploading active data stored in an actively managed database service. However, some data that may be relevant to identifying data trends may be stored in a backup system or may have been exported to another storage service. FIG. 4 depicts a technique for retrieving data from such a system.

A user may be provisioned a data transfer device 402, which may be a portable hard drive or other form of data storage. The data transfer device 402 may be preconfigured with a version of the uploader 314 already installed or may be configured to interface with the uploader 314. An example of a data transfer device 402 suitable for use with exemplary embodiments is the set of SNOW family of devices provided by AWS.

A user may copy their backups and exports 404 from their own storage onto the data transfer device 402, and then either run the uploader 314 on the data transfer device 402 or send the data transfer device 402 to another party for uploading.

In either event, the data transfer device 402 may be connected to a local data service 326 as shown in FIG. 3 and may execute a job to run the uploader 314. For each backup stored on the data transfer device 402, the data from the backup may be restored into the database 308 of the local data service 326. The uploader 314 may then be run on the restored data and pushed to the cloud storage service 332.

After the data is uploaded, the trending data module 328 may identify data trends and generate visualizations of the data. The trending data module 328 may be controlled through the visualization application 330. The visualization application 330 may initially display a home interface, such as the visualization interface 500 shown in FIG. 5.

The visualization interface 500 includes a module for selecting trend analyses 502 and a dashboards interface 508. An analysis refers to the basic workspace for creating visualizations, which are graphical representations of data. Each analysis may contain a collection of visualizations that a user can arrange and customize.

Figure 9A:
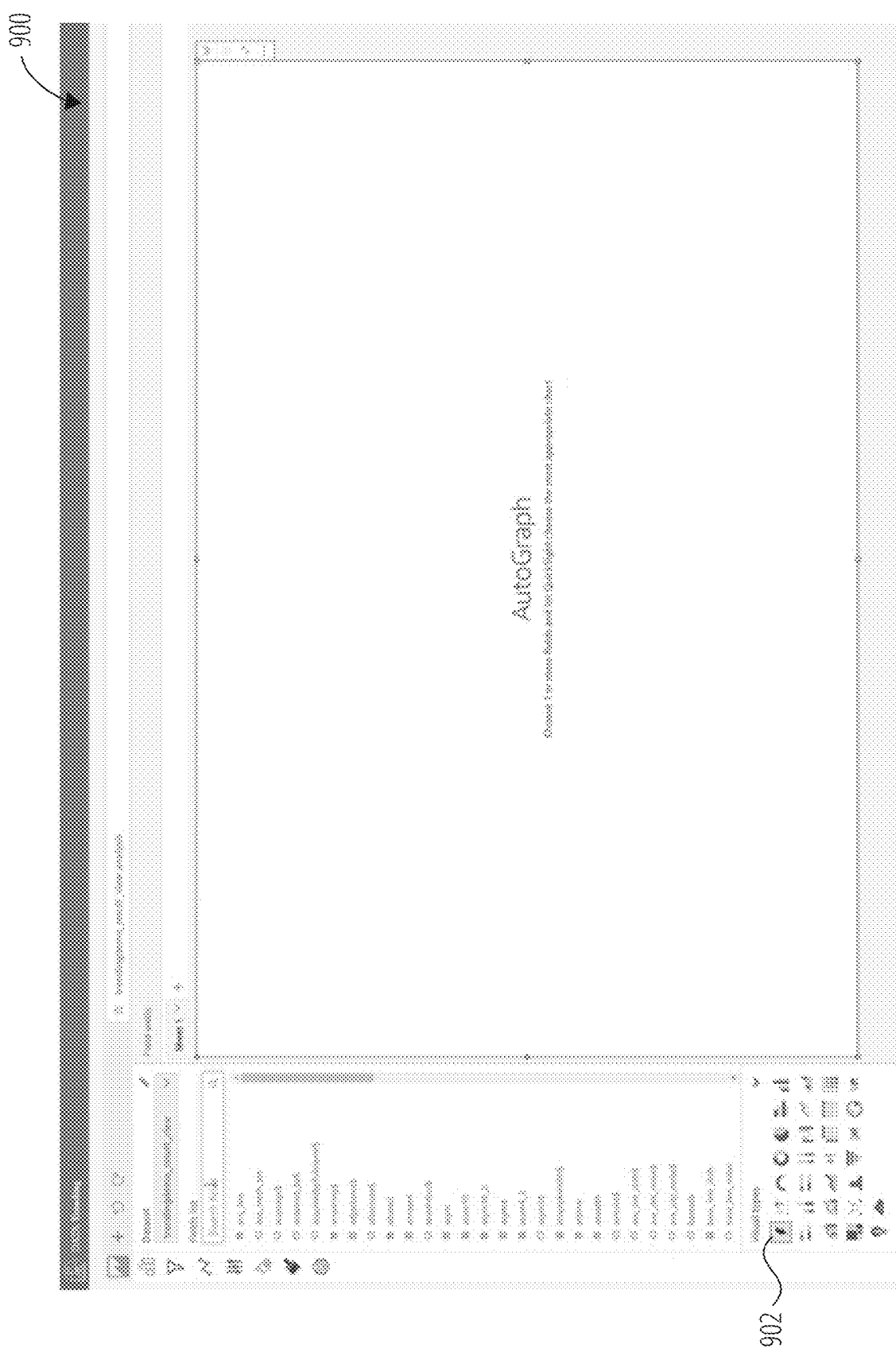
FIG. 9A-FIG. 9H illustrate various examples of visualization interfaces in accordance with exemplary embodiments.

A data visualization may be a diagram, chart, graph, table, etc. Data visualizations may begin in an AutoGraph mode in which the trending data module 328 attempts to select the best visualization configuration for the data based on the type of the data, fields present in the data, amount of the data, etc. An example of a visualization interface 900 showing the AutoGraph mode is shown in FIG. 9A.

A dashboard is the published version of an analysis that can be viewed by any user having access rights to the dashboard. It can be shared for reporting purposes. The sharing user may specify which other users have access, and what rights are provided as part of that access.

The trend analyses 502 module may include a new analysis element 504 and an existing analysis element 506. The new analysis element 504 may allow the user to create a new analysis by selecting data sets for inclusion in the analysis, selecting fields within the data sets that should be included in visualizations, customizing the visualizations, etc. Selecting the new analysis element 504 may cause an interface such as the one shown in FIG. 6 or FIG. 7 to be displayed.

Selecting the existing analysis element 506 may display an interface showing previously saved analyses. The most recently accessed analyses may also be displayed in the trend analyses 502 module. Similarly, the dashboards interface 508 may include interface elements corresponding to previously saved dashboards 510.

Figure 6:
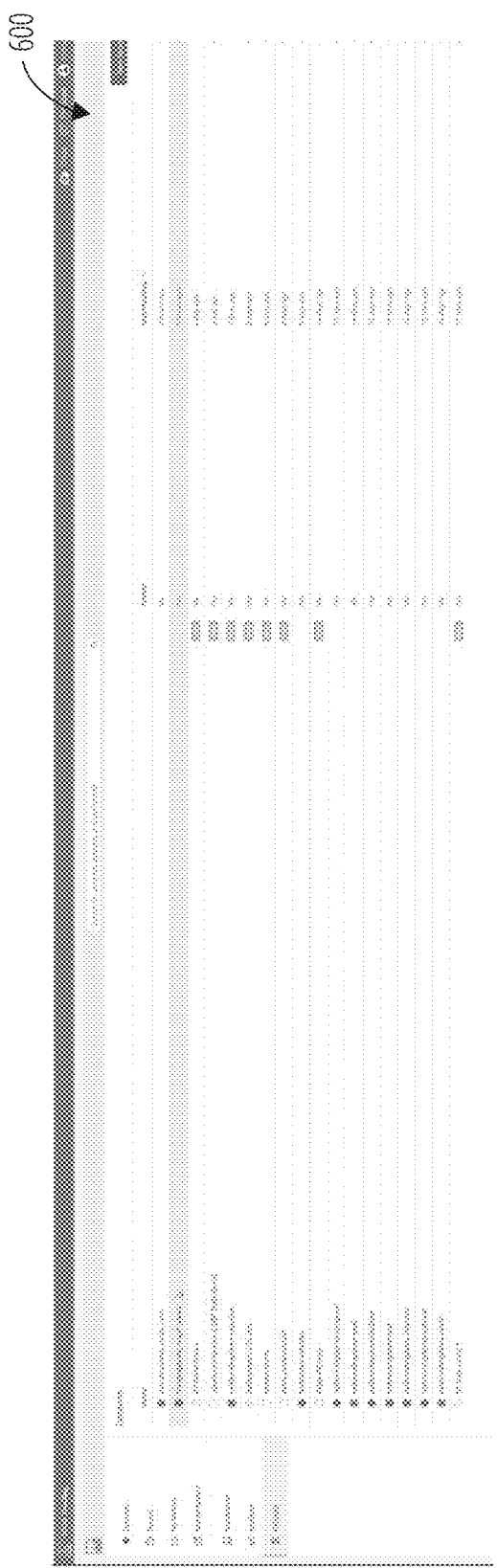
FIG. 6 illustrates a data set selection interface in accordance with one embodiment.

FIG. 6 depicts an example of a datasets interface 600 suitable for creating an analysis. The datasets interface 600 shows a list of available data sets, such as data sets that have been uploaded through the uploader 314. A user may select one or more data sets in the datasets interface 600 for inclusion in the analysis.

Figure 7:
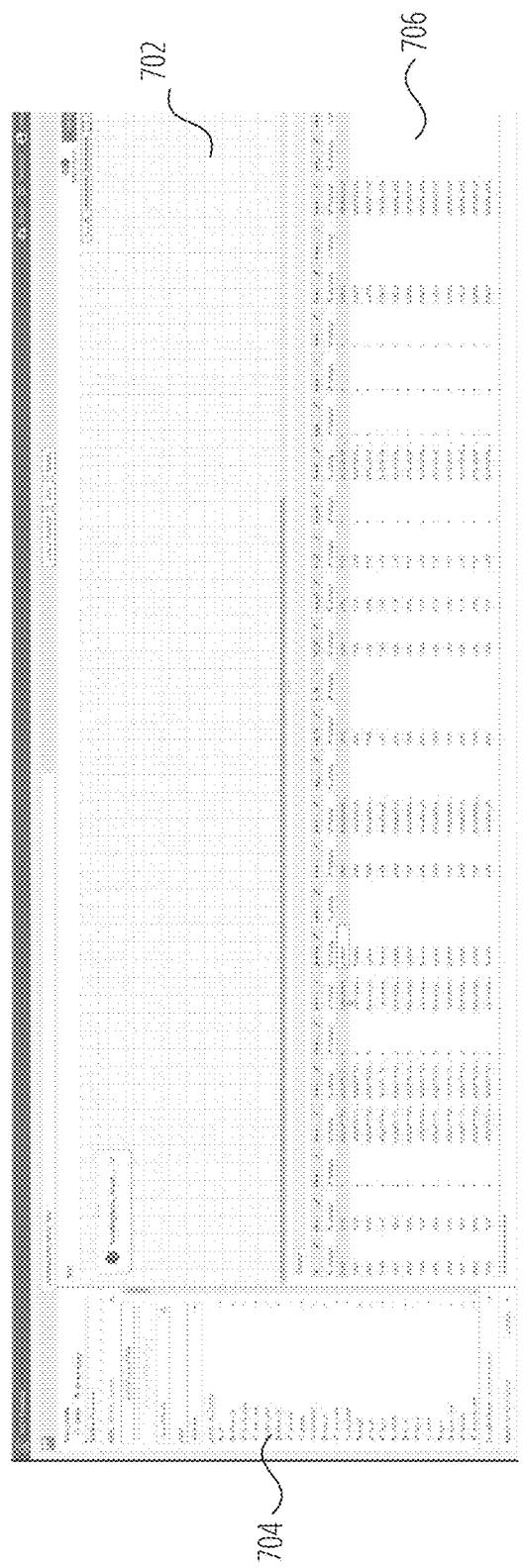
FIG. 7 illustrates an alternative data set selection interface in accordance with one embodiment.

Alternatively or in addition, a user may select data sets in an interface such as the one depicted in FIG. 7. The interface of FIG. 7 includes a datasets selector 706 similar to the data sets list depicted in FIG. 6. A user may select one or more data sets for inclusion in the analysis through the datasets selector 706.

Upon selecting one or more data sets, a list of fields 704 may be displayed in the interface. The fields 704 may include any fields that were defined for the data of the selected data sets. The user may select one or more fields 704 for inclusion in the analysis. Based on the data sets and fields selected, the trending data module 328 may determine an appropriate visualization and a preview of the visualization in a data view 702.

Figure 8:
FIG. 8 illustrates an example of a data visualization in accordance with one embodiment.

Upon selecting a group of data sets for inclusion in an analysis, an interface such as the one depicted in FIG. 8 may be displayed. The interface may include a dataset selector 802 showing the data sets that have currently been selected for display (and allowing the user to change those data sets, if desired). A fields menu 804 may also allow a list of fields from the data sets to be selected, similar to FIG. 7.

The interface also includes a set of visualization configurations 806, which represent preconfigured groups of settings that define how a particular configuration is displayed. For example, the visualization configurations 806 may include an element for displaying a line graph, bar graph, pie chart, etc. The interface may also allow the user to configure a visualization with custom settings and save the settings as a configuration for display in the visualization configurations 806.

The interface also includes a visualization 808, showing the data visualized according to the selected visualization configuration 806.

FIG. 9A—FIG. 9H depict various examples of the visualization interface 900. FIG. 9A in particular shows the AutoGraph interface, in which the trending data module 328 determines the best visualization settings based on the type and amount of data in selected data sets, and any fields that have been selected for visualization. The AutoGraph interface may be displayed by default. Furthermore, a user can return to the AutoGraph interface by selecting a corresponding automatic visualization element 902 in the visualization configurations 806.

As fields are selected in the fields menu 804, the trending data module 328 may analyze the currently selected fields to predict what type of analysis the user is attempting to perform (e.g., a method performance, a column performance, a product performance, a product stability, a system suitability, a site performance, a system performance, or an analyst performance). The trending data module 328 may then select an appropriate type of visualization, which may be a predetermined type of visualization associated with the analysis or a type of visualization determined through AI/ML analysis of previous visualization examples (e.g., as determined based on the fields selected).

Figure 9B:
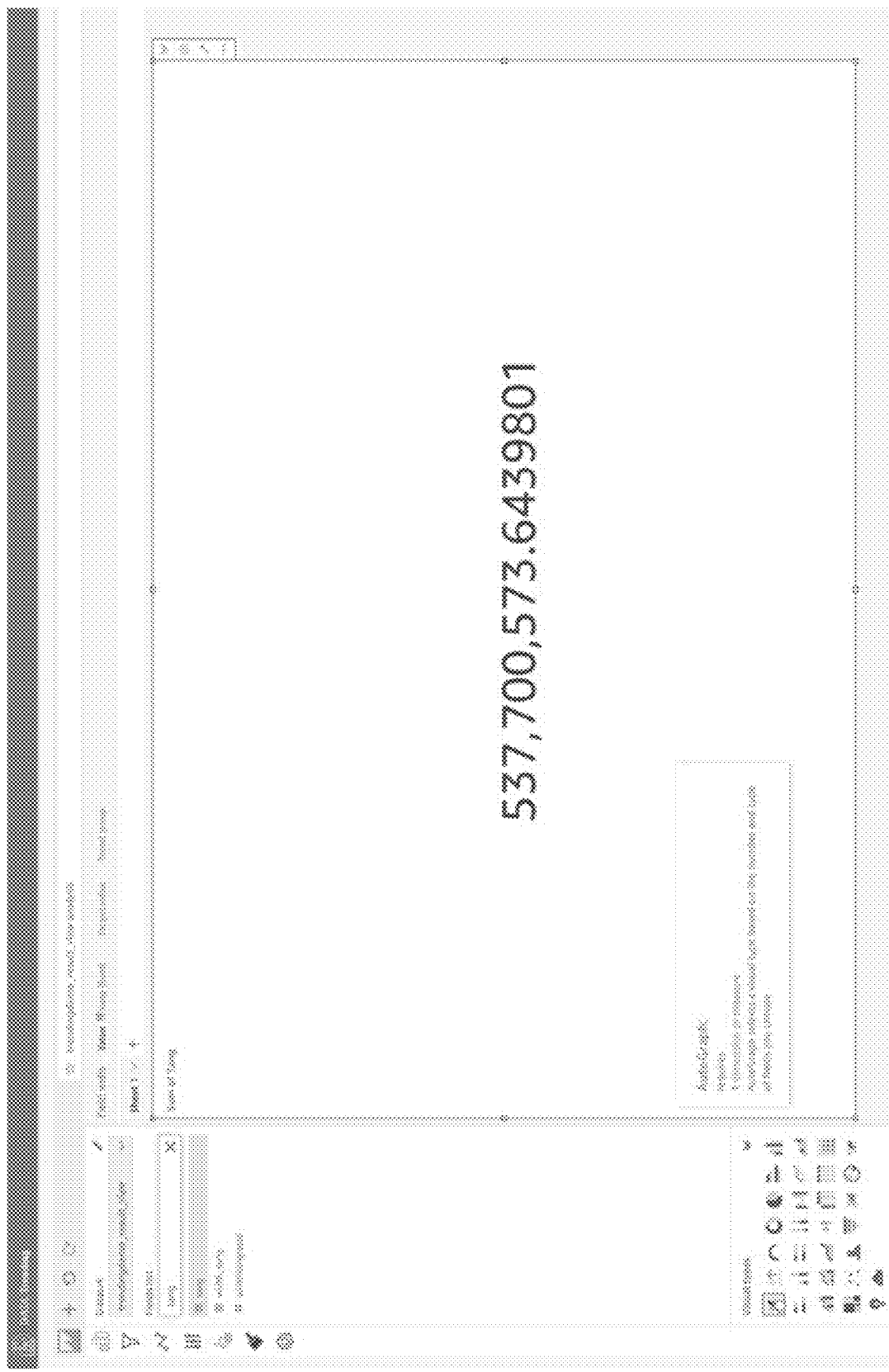

FIG. 9B depicts a type of visualization automatically selected for one-dimensional data. In this case, the user has selected a field in the fields menu having one-dimensional data values (the sum of a set of data values). Since the data is represented as a single data point, the value of the data point is displayed in the visualization interface.

Figure 9C:

If more data is added to the selected data sets over time, then the visualization may be updated as shown in FIG. 9C. In this example, the single data point of FIG. 9B has been supplemented with additional data, and the visualization has been automatically updated to display a line graph.

FIG. 9C further illustrates a filters tab 904, which allows the user to create filters to be applied to the selected fields and data sets. In the filters tab 904, a user can specify filtering conditions indicating which data should be included or excluded from the visualization. For example, a user might specify minimum and/or maximum values with which to filter the data.

Figure 9D:
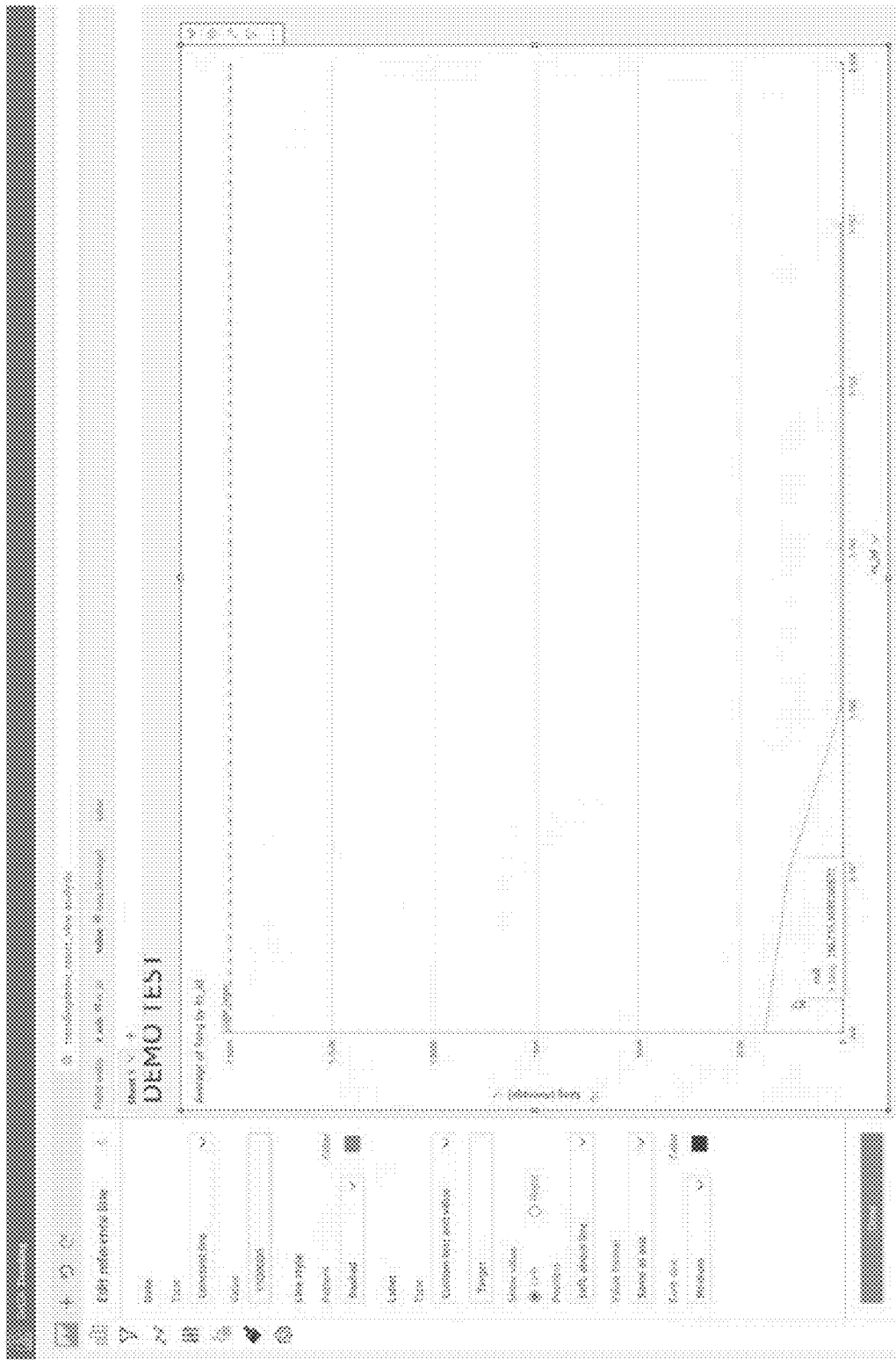

As demonstrated in FIG. 9D, users may also add additional visual elements to the visualization interface, such as reference lines. Using the interface, the user can define parameters such as a y-intercept and/or slope for the reference line, as well as other characteristics such as the weight, color, and style of the line.

Figure 9E:
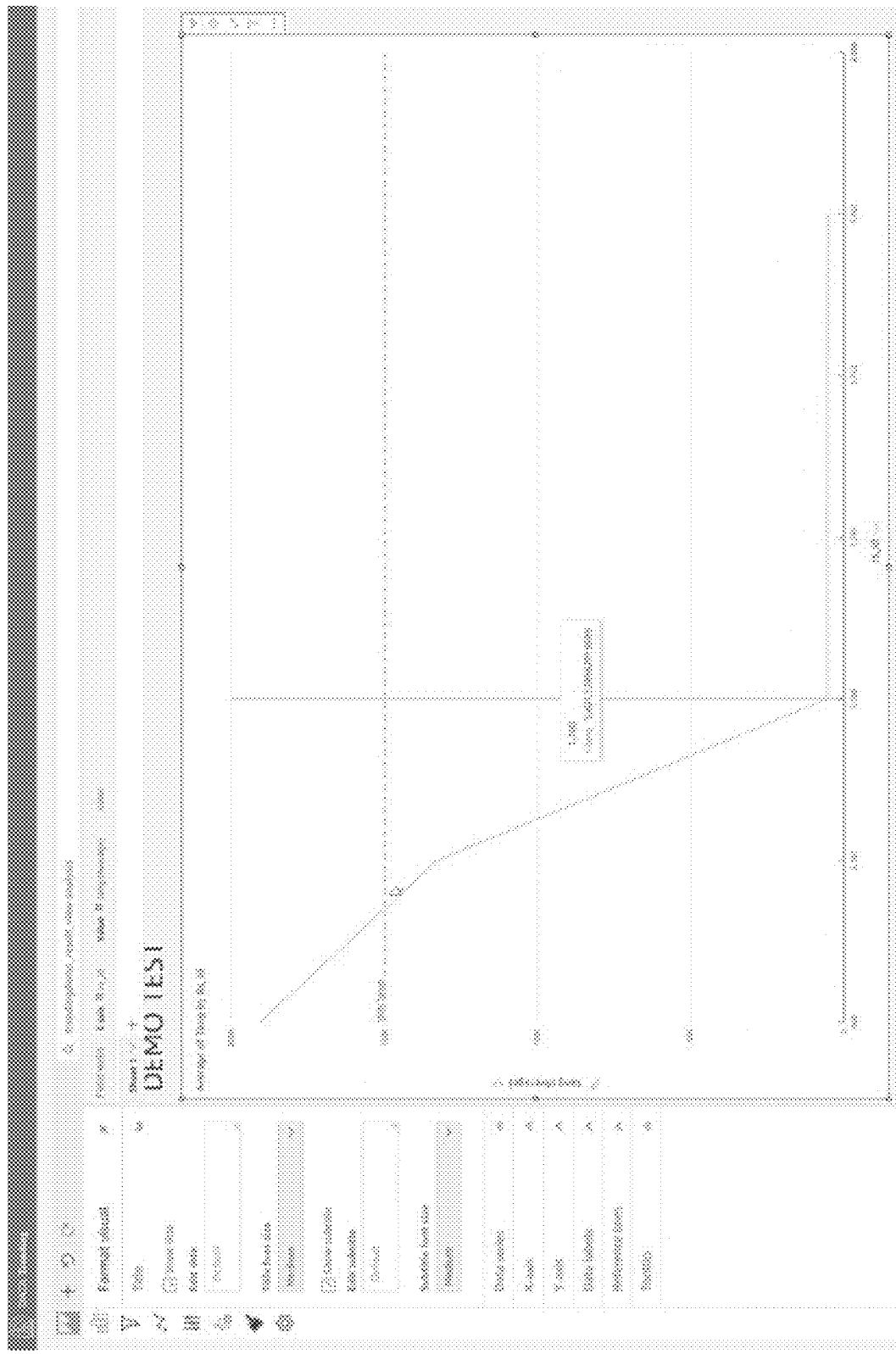
Figure 9F:
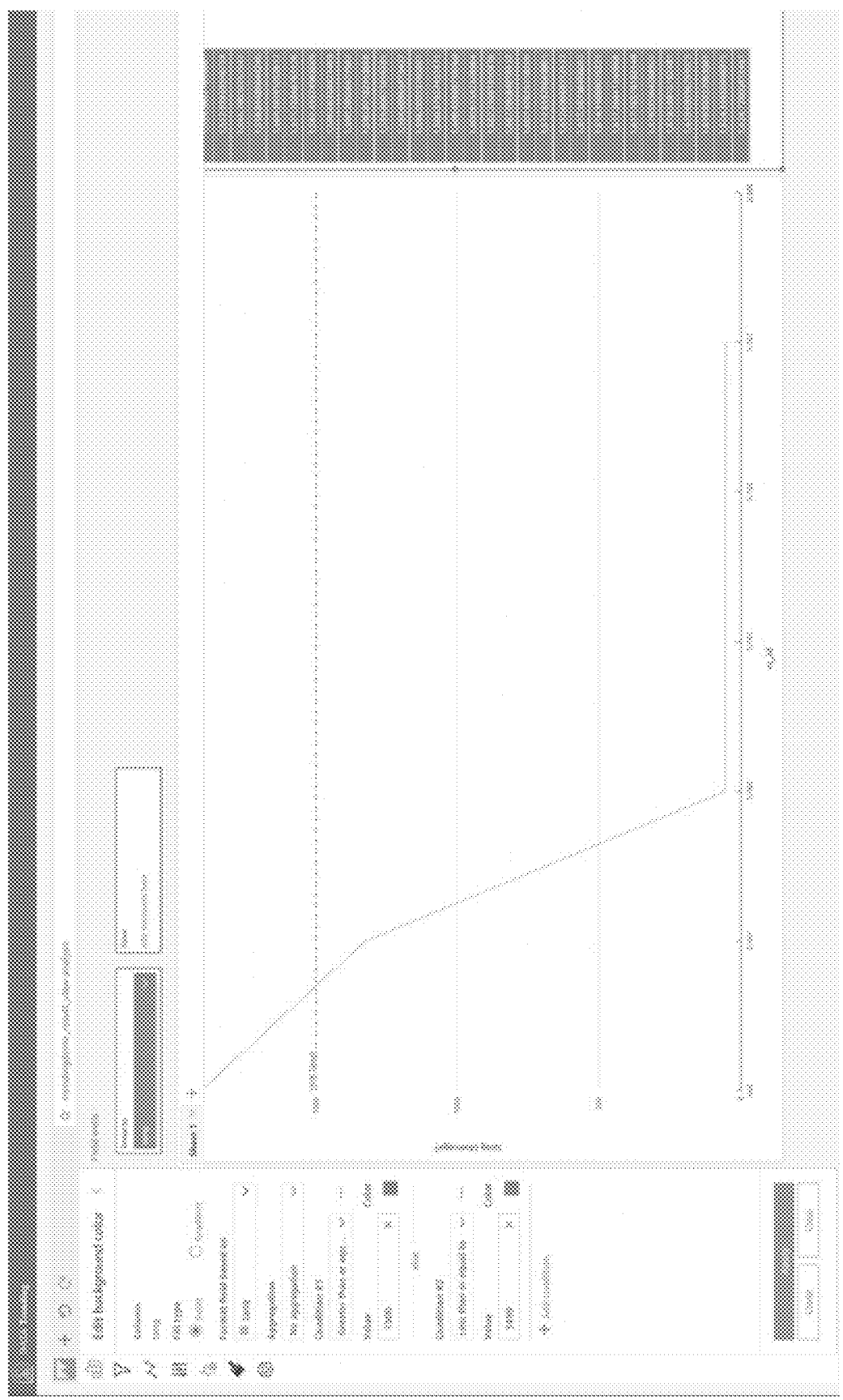

The user can also add titles, subtitles, and other text, as shown in FIG. 9E.

Furthermore, the user can display the data associated with the visualization, and set conditions to cause certain data points to be visually distinguished from other data points. For example, in FIG. 9F the user has applied a condition to color the background of the data cell green when the data value is equal to or above 1500, and red when below 1500.

Figure 9G:
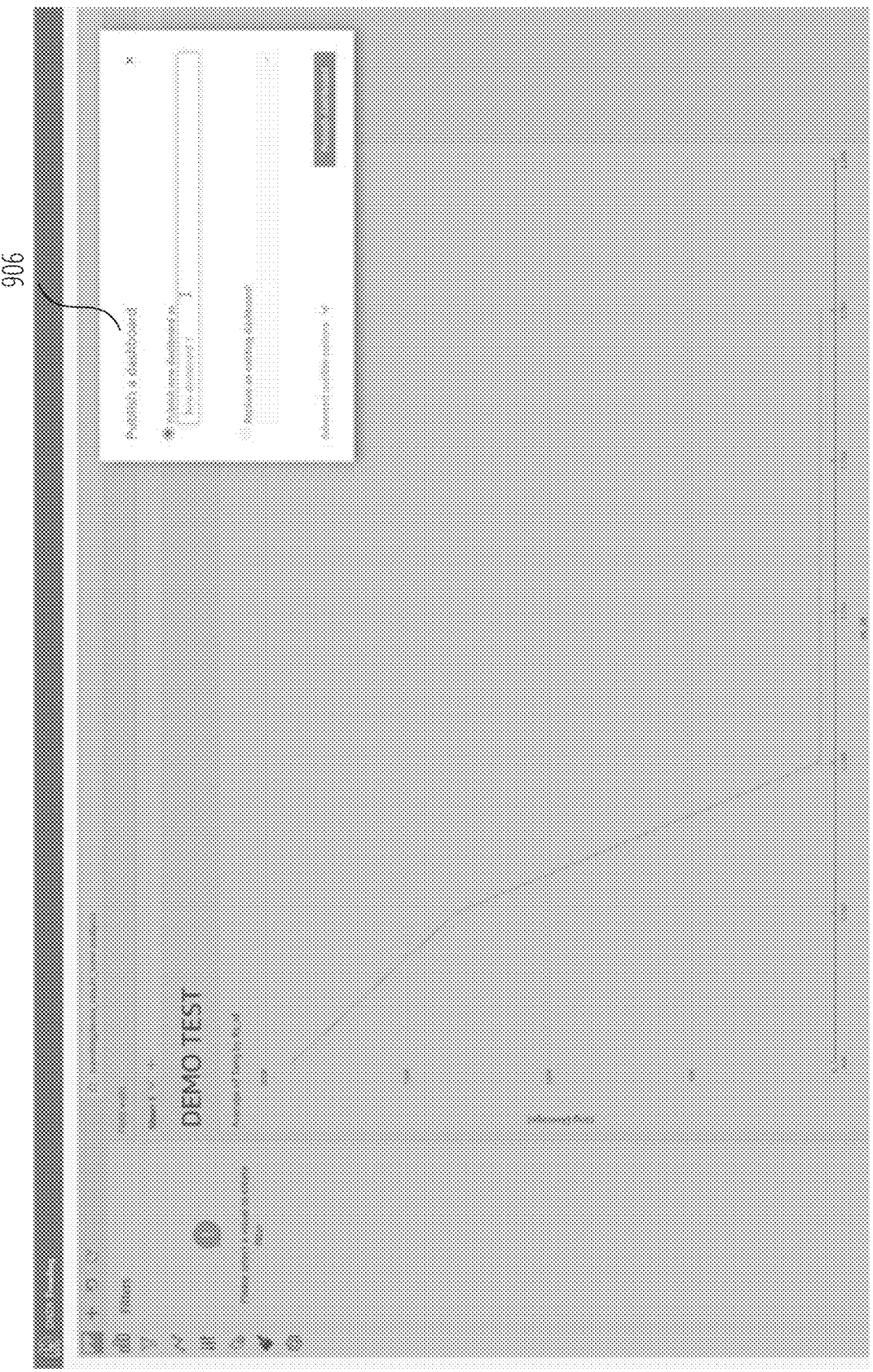
Figure 9H:
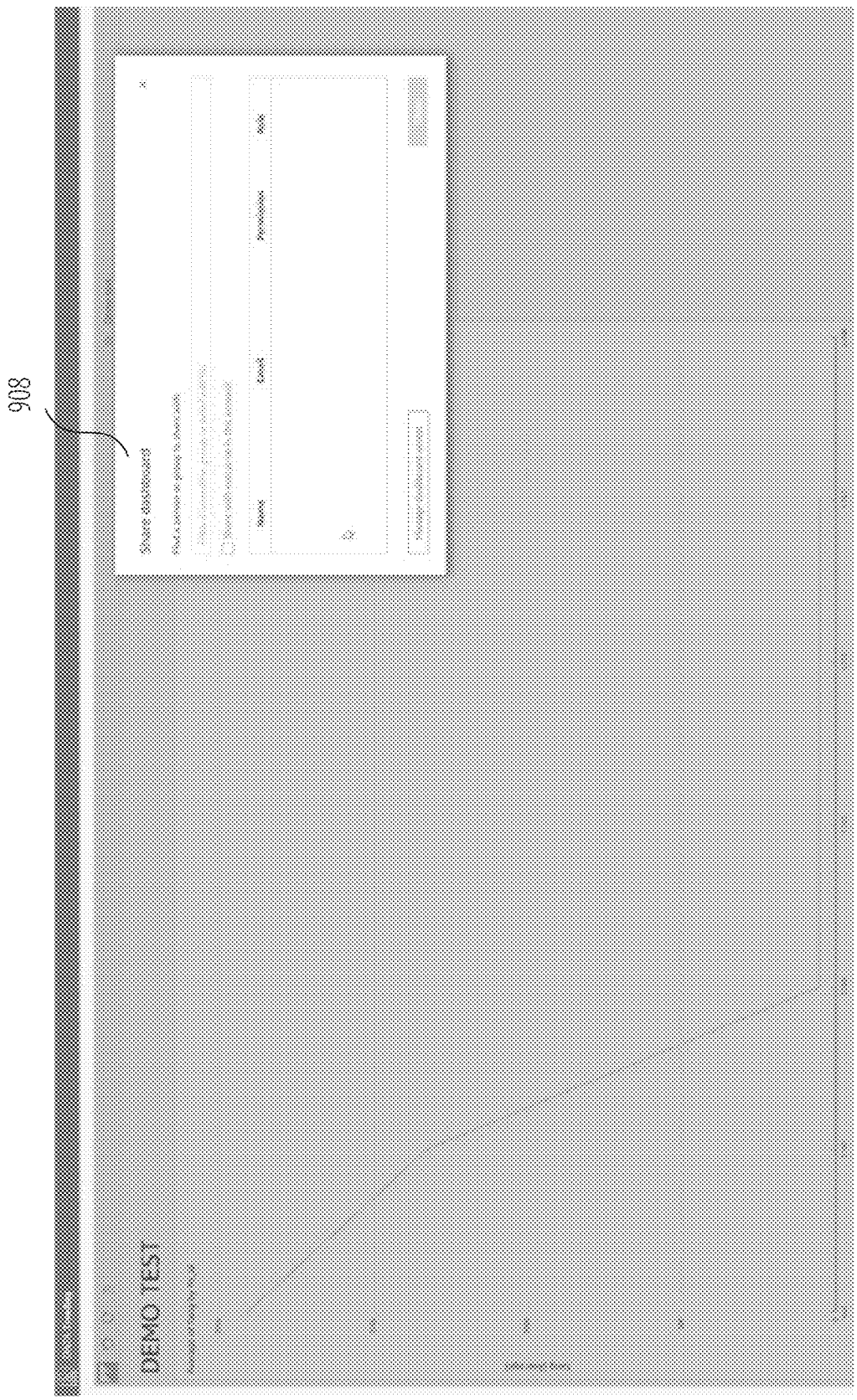

After the user is satisfied with a given visualization, they may optionally mark it as read-only. The visualization may be published to the visualization dashboard using a dashboard publication wizard 906, as shown in FIG. 9G, or may be shared with particular users or groups of users with a dashboard sharing wizard 908 as shown in FIG. 9H.

Figure 10:
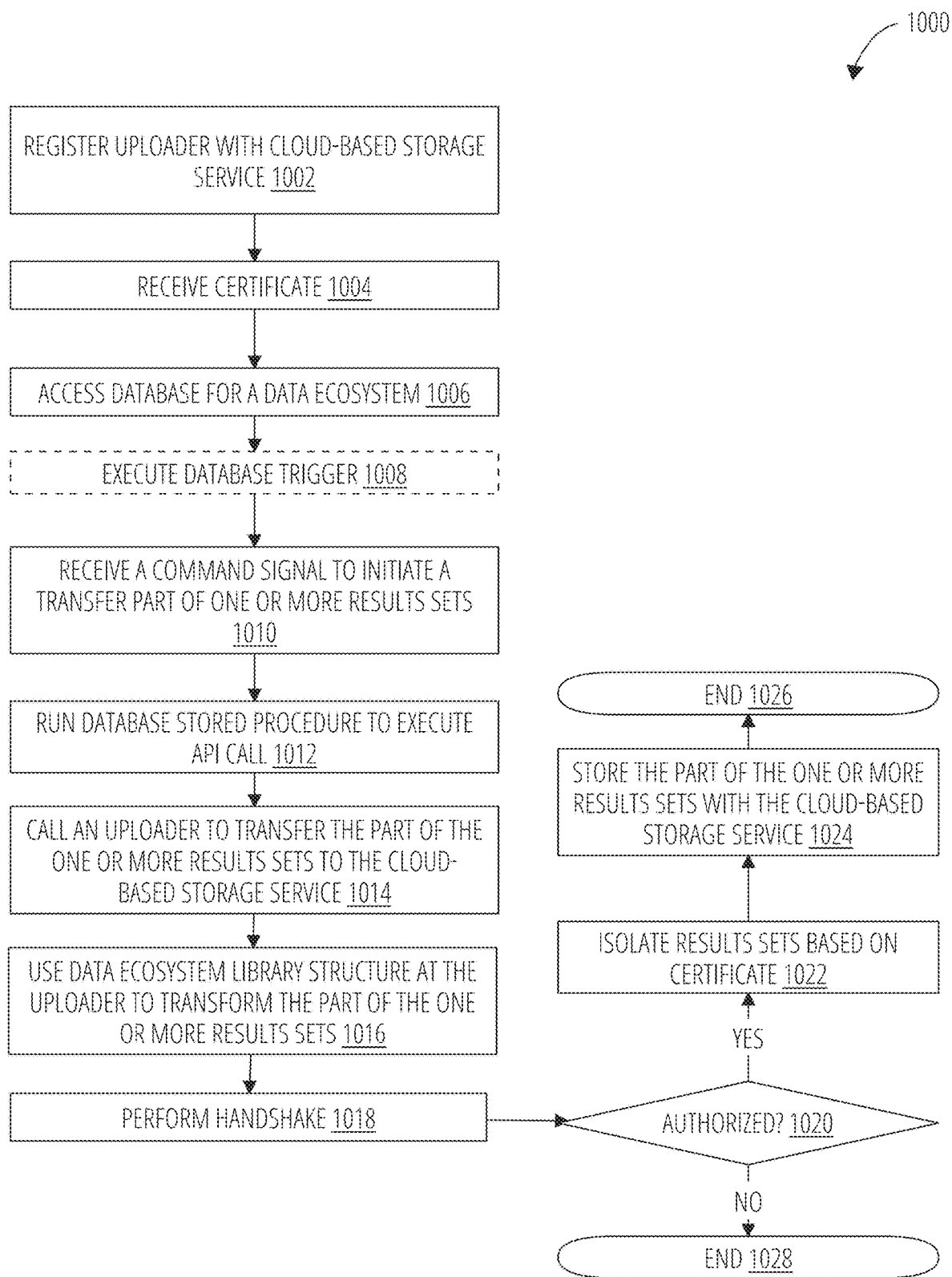
FIG. 10 illustrates exemplary data uploading logic in accordance with one embodiment.

FIG. 10 is a flowchart depicting exemplary data uploading logic for performing a computer-implemented method according to an exemplary embodiment. The logic may be embodied as instructions stored on a computer-readable medium configured to be executed by a processor. The logic may be implemented by a suitable computing system configured to perform the actions described below.

In block 1002, the system may receive an instruction to install a data uploader, and may register the uploader with cloud-based storage service. As part of registering the uploader, the user may authenticate themselves or their organization with the cloud-based storage service to verify that they have rights to use the uploader. They may also provide a tenancy identifier that identifies a particular tenancy that they are associated with in the cloud computing service.

In block 1004, the cloud computing service may authenticate the user or organization, and in response the system may receive a security certificate that is installed with the uploader.

In block 1006, the system may access database for a data ecosystem. The database may store data related to analytical chemistry experiments. The data may be organized into data sets or results sets, which may be associated with a particular experiment, and the data sets may be organized into projects. A project may be a user-defined collection of data sets. The data may include a number of values, each tagged with a field that describes what the data value represents. The data may be organized into a first data model for storage in the database. The data ecosystem may include one or more libraries that provide instructions for deserializing the first data model.

In block 1008, the system my optionally receive new data in a data set and, in response, execute a predefined database trigger. The predefined database trigger may, in block 1010, cause a command signal to be sent to the database's management system to initiate a transfer of part of one or more results sets. In block 1012, the database management system may run a database stored procedure to execute an API call to the uploader.

In block 1014, the API call may cause the uploader to transfer the part of the one or more results sets to the cloud-based storage service. In order to perform the transfer, at block 1016 the uploader may use its own copy of the deserializing libraries from the data ecosystem to deserialize the data. Accordingly, the uploader can be decoupled from the data ecosystem.

In block 1018, the uploader may perform a handshake with the cloud computing service by providing the security certificate received in block 1004 to the cloud computing service. In decision block 1020, the system may determine whether access is authorized by determining a validity of the security certificate. If access is not authorized (e.g., because the user's credentials are invalid or the user does not have access rights to use the uploader), then processing may proceed to done block 1028. The user may be informed that they do not have permission to install the uploader, and processing may terminate.

If access is authorized, processing may proceed to block 1022. In block 1022, the cloud storage service may isolate the uploaded results sets to a particular tenancy based on the tenancy identifier associated with the certificate. The tenancy identifier may be provided as metadata as part of the data upload.

In block 1024, the system may store the part of the one or more results sets with the cloud-based storage service. This may involve applying an ETL service to transform the data into a second data model that is consistent with a data warehouse of the cloud-based storage service. Processing may then proceed to done block 1026 and terminate.

Although FIG. 10 depicts particular actions performed in a specific order, embodiments are not limited to the configuration shown in FIG. 10. It is contemplated that more, fewer, or different logical blocks may be implemented. Similarly, it is contemplated that the actions may be performed in a different order than the one shown in FIG. 10.

Figure 11:
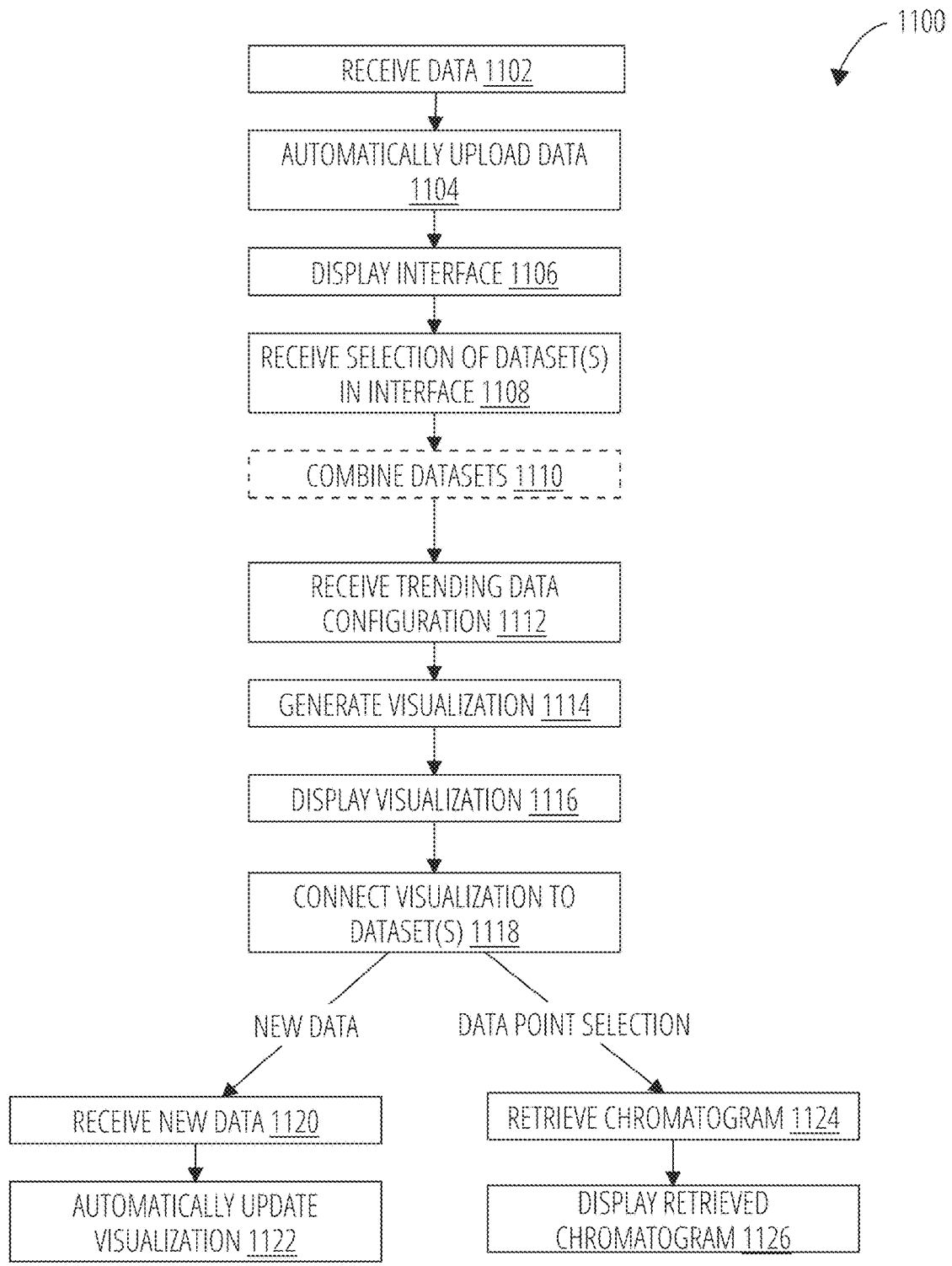
FIG. 11 illustrates exemplary data visualization logic in accordance with one embodiment.

FIG. 11 is a flowchart depicting exemplary data visualization logic for performing a computer-implemented method according to an exemplary embodiment. The logic may be embodied as instructions stored on a computer-readable medium configured to be executed by a processor. The logic may be implemented by a suitable computing system configured to perform the actions described below.

In block 1102, the system may receive data associated with an analytical chemistry system. For example, the data may be existing data stored in a database, may be newly received data, may be archived or backup data, etc. In block 1104, the system may automatically upload the data to a cloud-based storage system. The data may be uploaded using the procedure described above in FIG. 10.

In block 1106, the system may display a visualization interface, such as the interface depicted in FIG. 6 through FIG. 9H. The interface may include a dataset selector allowing the user to select one or more data sets from the data for visualization in block 1108.

If more than one data set is selected in block 1108, then in block 1110 the system may optionally combine datasets into a single data set for visualization. Alternatively or in addition, the system may overlay one data set on top of another in the visualization, such as by displaying different lines for each data set in a line graph.

In block 1112, the system may receive a trending data configuration. The configuration may describe a type of visualization to be applied to the data, as well as (optionally) other visual elements for the visualization. These elements might include, for example, reference lines, explanatory text, titles or subtitles, etc.

In block 1114, the system may generate a visualization based on the selected data and the trending data configuration. The visualization may be displayed in block 1116.

In block 1118, the visualization may be connected to the selected dataset(s). For example, a flag may be set in the visualization's configuration data that indicates which data sets are associated with the visualization. The flag may indicate that the visualization should be updated at predetermined intervals, which may depend on the type of analysis being performed. For example, analyst performance may be measured as part of a yearly review, and therefore an analyst performance analysis only needs to be updated on a yearly basis. On the other hand, performance of a given lab might be evaluated quarterly, so a site analysis might be updated on a quarterly basis. Individual instrument performance might need to be checked monthly or even daily, and so could be updated on that basis. When the predetermined interval expires, the visualization may be updated with any new data received during the interval.

Alternatively or in addition, the flag may indicate that the visualization should be updated in real time. In this case, in block 1120 the system may register the receipt of new data in the data sets associated with the visualization. For example, the trending data module 328 may receive a notification from the data warehouse 322 that the data warehouse 322 has received new data. In block 1122, the trending data module 328 may automatically update the visualization with the new data.

The system might also receive an instruction to zoom in on particular data in the data set, such as by receiving a selection of a particular data point in the visualization. In response, at block 1124 the system may retrieve the raw data associated with the selected data point, which may be in the form of a chromatogram. In block 1126, the system may display the retrieved raw data in the visualization interface.

Although FIG. 11 depicts particular actions performed in a specific order, embodiments are not limited to the configuration shown in FIG. 11. It is contemplated that more, fewer, or different logical blocks may be implemented. Similarly, it is contemplated that the actions may be performed in a different order than the one shown in FIG. 11.

FIG. 12 illustrates one example of a system architecture and data processing device that may be used to implement one or more illustrative aspects described herein in a stand-alone and/or networked environment. Various network nodes, such as the data server 1210, web server 1206, computer 1204, and laptop 1202 may be interconnected via a wide area network 1208 (WAN), such as the internet. Other networks may also or alternatively be used, including private intranets, corporate networks, LANs, metropolitan area networks (MANs) wireless networks, personal networks (PANs), and the like. Network 1208 is for illustration purposes and may be replaced with fewer or additional computer networks. A local area network (LAN) may have one or more of any known LAN topology and may use one or more of a variety of different protocols, such as ethernet. Devices data server 1210, web server 1206, computer 1204, laptop 1202 and other devices (not shown) may be connected to one or more of the networks via twisted pair wires, coaxial cable, fiber optics, radio waves or other communication media.

Computer software, hardware, and networks may be utilized in a variety of different system environments, including standalone, networked, remote-access (aka, remote desktop), virtualized, and/or cloud-based environments, among others.

The term "network" as used herein and depicted in the drawings refers not only to systems in which remote storage devices are coupled together via one or more communication paths, but also to stand-alone devices that may be coupled, from time to time, to such systems that have storage capability. Consequently, the term "network" includes not only a "physical network" but also a "content network," which is comprised of the data—attributable to a single entity—which resides across all physical networks.

The components may include data server 1210, web server 1206, and client computer 1204, laptop 1202. Data server 1210 provides overall access, control and administration of databases and control software for performing one or more illustrative aspects described herein. Data server-data server 1210 may be connected to web server 1206 through which users interact with and obtain data as requested. Alternatively, data server 1210 may act as a web server itself and be directly connected to the internet. Data server 1210 may be connected to web server 1206 through the network 1208 (e.g., the internet), via direct or indirect connection, or via some other network. Users may interact with the data server 1210 using remote computer 1204, laptop 1202, e.g., using a web browser to connect to the data server 1210 via one or more externally exposed web sites hosted by web server 1206. Client computer 1204, laptop 1202 may be used in concert with data server 1210 to access data stored therein, or may be used for other purposes. For example, from client computer 1204, a user may access web server 1206 using an internet browser, as is known in the art, or by executing a software application that communicates with web server 1206 and/or data server 1210 over a computer network (such as the internet).

Servers and applications may be combined on the same physical machines, and retain separate virtual or logical addresses, or may reside on separate physical machines. FIG. 12 illustrates just one example of a network architecture that may be used, and those of skill in the art will appreciate that the specific network architecture and data processing devices used may vary, and are secondary to the functionality that they provide, as further described herein. For example, services provided by web server 1206 and data server 1210 may be combined on a single server.

Each component data server 1210, web server 1206, computer 1204, laptop 1202 may be any type of known computer, server, or data processing device. Data server 1210, e.g., may include a processor 1212 controlling overall operation of the data server 1210. Data server 1210 may further include RAM 1216, ROM 1218, network interface 1214, input/output interfaces 1220 (e.g., keyboard, mouse, display, printer, etc.), and memory 1222. Input/output interfaces 1220 may include a variety of interface units and drives for reading, writing, displaying, and/or printing data or files. Memory 1222 may further store operating system software 1224 for controlling overall operation of the data server 1210, control logic 1226 for instructing data server 1210 to perform aspects described herein, and other application software 1228 providing secondary, support, and/or other functionality which may or may not be used in conjunction with aspects described herein. The control logic may also be referred to herein as the data server software control logic 1226. Functionality of the data server software may refer to operations or decisions made automatically based on rules coded into the control logic, made manually by a user providing input into the system, and/or a combination of automatic processing based on user input (e.g., queries, data updates, etc.).

Memory 1222 (deleted) may also store data used in performance of one or more aspects described herein, including a first database 1232 and a second database 1230. In some embodiments, the first database may include the second database (e.g., as a separate table, report, etc.). That is, the information can be stored in a single database, or separated into different logical, virtual, or physical databases, depending on system design. Web server 1206, computer 1204, laptop 1202 may have similar or different architecture as described with respect to data server 1210. Those of skill in the art will appreciate that the functionality of data server 1210 (or web server 1206, computer 1204, laptop 1202) as described herein may be spread across multiple data processing devices, for example, to distribute processing load across multiple computers, to segregate transactions based on geographic location, user access level, quality of service (QOS), etc.

One or more aspects may be embodied in computer-usable or readable data and/or computer-executable instructions, such as in one or more program modules, executed by one or more computers or other devices as described herein. Generally, program modules include routines, programs, objects, components, data structures, etc. that perform particular tasks or implement particular abstract data types when executed by a processor in a computer or other device. The modules may be written in a source code programming language that is subsequently compiled for execution or may be written in a scripting language such as (but not limited to) HTML or XML. The computer executable instructions may be stored on a computer readable medium such as a nonvolatile storage device. Any suitable computer readable storage media may be utilized, including hard disks, CD-ROMs, optical storage devices, magnetic storage devices, and/or any combination thereof. In addition, various transmission (non-storage) media representing data or events as described herein may be transferred between a source and a destination in the form of electromagnetic waves traveling through signal-conducting media such as metal wires, optical fibers, and/or wireless transmission media (e.g., air and/or space). various aspects described herein may be embodied as a method, a data processing system, or a computer program product. Therefore, various functionalities may be embodied in whole or in part in software, firmware and/or hardware or hardware equivalents such as integrated circuits, field programmable gate arrays (FPGA), and the like. Particular data structures may be used to more effectively implement one or more aspects described herein, and such data structures are contemplated within the scope of computer executable instructions and computer-usable data described herein.

The components and features of the devices described above may be implemented using any combination of discrete circuitry, application specific integrated circuits (ASICs), logic gates and/or single chip architectures. Further, the features of the devices may be implemented using microcontrollers, programmable logic arrays and/or microprocessors or any combination of the foregoing where suitably appropriate. It is noted that hardware, firmware and/or software elements may be collectively or individually referred to herein as "logic" or "circuit."

It will be appreciated that the exemplary devices shown in the block diagrams described above may represent one functionally descriptive example of many potential implementations. Accordingly, division, omission or inclusion of block functions depicted in the accompanying figures does not infer that the hardware components, circuits, software and/or elements for implementing these functions would be necessarily be divided, omitted, or included in embodiments.

At least one computer-readable storage medium may include instructions that, when executed, cause a system to perform any of the computer-implemented methods described herein.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

With general reference to notations and nomenclature used herein, the detailed descriptions herein may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Various embodiments also relate to apparatus or systems for performing these operations. This apparatus may be specially constructed for the required purpose or it may comprise a general-purpose computer as selectively activated or reconfigured by a computer program stored in the computer. The procedures presented herein are not inherently related to a particular computer or other apparatus. Various general-purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

What is claimed is:

1. A computer-implemented method comprising:
   receiving data associated with an analytical chemistry system;
   automatically uploading the data to a cloud-based storage service;
   receiving a selection of a dataset in a visualization interface, the uploaded data incorporated into the selected dataset;
   determining a configuration of a trending data setting for the dataset, wherein determining the configuration comprises:
      examining, using a trending data module, a type and amount of data included in the selected dataset, and
      automatically determining, based on the examining and by the trending data module, the configuration for the trending data setting;
   generating a visualization of the dataset based on the trending data setting configuration; and
   displaying the visualization in a visualization dashboard.

2. The computer-implemented method of claim 1, wherein the visualization displays one or more of: a method performance, a column performance, a product performance, a product stability, a system flexibility, a system usage, a system suitability, a site performance, a system performance, or an analyst performance.

3. The computer-implemented method of claim 1, wherein the dataset is a first dataset associated with a first analytical chemistry project, and further comprising:
   receiving a selection of a second dataset from a second analytical chemistry project in the visualization interface;
   combining the first dataset and the second dataset to create a combined dataset; and
   generating a visualization of the combined dataset.

4. The computer-implemented method of claim 1, further comprising:
   connecting the visualization dashboard to the dataset;
   receiving new data in the dataset; and
   automatically updating the visualization with the new data.

5. The computer-implemented method of claim 1, further comprising:
   displaying an interactive control element in the visualization interface, the interactive control element associated with a predefined configuration of settings or filters;
   receiving a selection of the interactive control element; and
   updating the visualization based on the predefined configuration.

6. The computer-implemented method of claim 1, wherein the visualization includes a plot made up of a plurality of data points, and further comprising:
   receiving a selection of one of the plurality of data points;
   retrieving a chromatogram associated with the selected data point; and
   displaying the retrieved chromatogram in the visualization dashboard.

7. The computer-implemented method of claim 1, wherein the dataset is a first dataset, further comprising:
   receiving a selection of a second dataset; and
   overlaying the second dataset on the first dataset in the visualization interface.

8. A non-transitory computer-readable storage medium, the computer-readable storage medium including instructions that when executed by a computer, cause the computer to:
   receive data associated with an analytical chemistry system;
   automatically upload the data to a cloud-based storage service;
   determine a configuration of a trending data setting for the dataset, wherein determining the configuration comprises:
      examining, using a trending data module, a type and amount of data included in the selected dataset, and
      automatically determining, based on the examining and by the trending data module, the configuration for the trending data setting;
   receive a configuration of a trending data setting for the dataset;
   generate a visualization of the dataset based on the trending data setting configuration; and
   display the visualization in a visualization dashboard.

9. The computer-readable storage medium of claim 8, wherein the visualization displays one or more of: a method performance, a column performance, a product performance, a product stability, a system flexibility, a system usage, a system suitability, a site performance, a system performance, or an analyst performance.

10. The computer-readable storage medium of claim 8, wherein the dataset is a first dataset associated with a first analytical chemistry project, and wherein the instructions further configure the computer to:
    receive a selection of a second dataset from a second analytical chemistry project in the visualization interface;
    combine the first dataset and the second dataset to create a combined dataset; and
    generate a visualization of the combined dataset.

11. The computer-readable storage medium of claim 8, wherein the instructions further configure the computer to:
connect the visualization dashboard to the dataset;
receive new data in the dataset; and
automatically update the visualization with the new data.

12. The computer-readable storage medium of claim 8, wherein the instructions further configure the computer to:
display an interactive control element in the visualization interface, the interactive control element associated with a predefined configuration of settings or filters;
receive a selection of the interactive control element; and
update the visualization based on the predefined configuration.

13. The computer-readable storage medium of claim 8, wherein the visualization includes a plot made up of a plurality of data points, and wherein the instructions further configure the computer to:
receive a selection of one of the plurality of data points;
retrieve a chromatogram associated with the selected data point; and
display the retrieved chromatogram in the visualization dashboard.

14. The computer-readable storage medium of claim 8, wherein the dataset is a first dataset, wherein the instructions further configure the computer to:
receive a selection of a second dataset; and
overlay the second dataset on the first dataset in the visualization interface.

15. A computing apparatus comprising:
a processor; and
a memory storing instructions that, when executed by the processor, configure the apparatus to:
receive data associated with an analytical chemistry system;
automatically upload the data to a cloud-based storage service;
receive a selection of a dataset in a visualization interface, the uploaded data incorporated into the selected dataset;
determine a configuration of a trending data setting for the dataset, wherein determining the configuration comprises:
examining, using a trending data module, a type and amount of data included in the selected dataset, and
automatically determining, based on the examining and by the trending data module, the configuration for the trending data setting;
generate a visualization of the dataset based on the trending data setting configuration; and
display the visualization in a visualization dashboard.

16. The computing apparatus of claim 15, wherein the visualization displays one or more of: a method performance, a column performance, a product performance, a product stability, a system flexibility, a system usage, a system suitability, a site performance, a system performance, or an analyst performance.

17. The computing apparatus of claim 15, wherein the dataset is a first dataset associated with a first analytical chemistry project, and wherein the instructions further configure the apparatus to:
receive a selection of a second dataset from a second analytical chemistry project in the visualization interface;
combine the first dataset and the second dataset to create a combined dataset; and
generate a visualization of the combined dataset.

18. The computing apparatus of claim 15, wherein the instructions further configure the apparatus to:
connect the visualization dashboard to the dataset;
receive new data in the dataset; and
automatically update the visualization with the new data.

19. The computing apparatus of claim 15, wherein the instructions further configure the apparatus to:
display an interactive control element in the visualization interface, the interactive control element associated with a predefined configuration of settings or filters;
receive a selection of the interactive control element; and
update the visualization based on the predefined configuration.

20. The computing apparatus of claim 15, wherein the visualization includes a plot made up of a plurality of data points, and wherein the instructions further configure the apparatus to:
receive a selection of one of the plurality of data points;
retrieve a chromatogram associated with the selected data point; and
display the retrieved chromatogram in the visualization dashboard.

* * * * *